(12) United States Patent
Wellstein

(10) Patent No.: US 7,528,109 B2
(45) Date of Patent: May 5, 2009

(54) PLEIOTROPHIN GROWTH FACTOR RECEPTOR FOR THE TREATMENT OF PROLIFERATIVE, VASCULAR AND NEUROLOGICAL DISORDERS

(75) Inventor: Anton Wellstein, Washington, DC (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/880,097

(22) Filed: Jun. 14, 2001

(65) Prior Publication Data

US 2002/0034768 A1    Mar. 21, 2002

Related U.S. Application Data

(60) Provisional application No. 60/211,491, filed on Jun. 14, 2000.

(51) Int. Cl.
    C07K 14/71   (2006.01)
    C07K 19/00   (2006.01)
    C07K 14/47   (2006.01)
    A61K 38/17   (2006.01)
(52) U.S. Cl. ........................... 514/12; 530/324
(58) Field of Classification Search ............ 530/300, 530/350
    See application file for complete search history.

(56) References Cited

U.S. PATENT DOCUMENTS 5,770,421 A    6/1998    Morris et al.
6,696,548 B2   2/2004    Morris et al.

FOREIGN PATENT DOCUMENTS

WO    00/20869         4/2000
WO    WO-01/96394 A2   12/2001
WO    WO-01/96394 A3   12/2001

OTHER PUBLICATIONS

Wells (Sep. 18, 1990) "Additivity of Mutational Effects in Proteins." Biochemistry 29(37): 8509-8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 433-506.*
Bork (2000) "Powers and Pitfalls in Sequence Analysis: The 70% Hurdle." Genome Research 10:398-400.*
Skolnick and Fetrow (2000) "From gene to protein structure and function: novel applications of computational approaches in th genomic era." Trends in Biotech. 18(1): 34-39.*
Doerks et al. (Jun. 1998) "Protein annotation: detective work for function prediction." Trends in Genetics 14(6): 248-250.*
Smith and Zhang (Nov. 1997) "The challenges of genome sequence annotation or 'The devil is in the details'." Nature Biotechnology 15:1222-1223.*
Brenner (Apr. 1999) "Errors in genome annotation." Trends in Genetics 15(4): 132-133.*
Bork and Bairoch (Oct. 1996) "Go hunting in sequence databases but watch out for the traps." Trends in Genetics 12(10): 425-427.*
Meng et al. (Mar. 14, 2000) "Pleiotrophin signals increased tyrosine phosphorylation of b-catenin through inactivation of the intrinsic catalytic activity of the receptor-type protein tyrosine phosphatase b/z." PNAS 97(6): 2603-2608.*
Maeda et al. (Apr. 30, 1999) "A Receptor-like Protein-tyrosine Phosphatase PTPx/RPTPb Binds a Heparin-binding Growth Factor Midkine." The Journal of Biological Chemistry 274(18): 12474-12479.*
Zhang et al., 1999. Proc Natl Acad Sci USA 96:6734-6738.*
Weber at al. 2000. Cancer Research 60:5284-5288.*
Ausbel et al. 1997. Short Protocols in Molecular Bioogy, pp. 10.82-10.84 and 11.23-11.25.*
Science Direct website printout for Caughey et al., one page, accessed Oct. 17, 2006.*
Pulford 1997. Blood 89:1394-1404.*
Lo et al. 1998. Protein Engineering 11:495-500.*
Sato 1999 Experimental Cell Research 246:152-164.*
Dreyfus 1998 Experimental Cell Research 241:171-180.*
Kung Meng et al., (Pleiotrophin signals increased tyrosine phosphorylation of b-catenin through inactivation of the intrinsic catalytic activity of the receptor-type protein tyrosine phosphatase B/ζ) Mar. 14, 2000, vol. 97 No. 6 pp. 2603-2608.
Nobuaki Maeda et al., ( A Receptor-like Protein-tyrosine Phosphate PTP/RPTPB Binds a Heparin-binding Growth Factor Midkine) vol. 274, No. 18. Apr. 30, 1999, pp. 12747-12479.
Nobuaki Maeda et al., (6B4 Proteoglycan/Phosphacan, an Extracellular Variant of Receptor-like Protein-tyrosine Phosphatase RPTPB, Binds Pleiotrophin/Heparin-binding Growth-associated Molecule (HB-GAM)* vol. 271, No. 35, Aug. 30, 1996, pp. 21446-21452.
Erkki Raulo et al., (Isolation of a Neuronal Cell Surface Receptor of Heparin Binding Growth-associated Molecule (HB-GAM) vol. 269, No. 17, Apr. 29, 1994, pp. 12999-13004.
K. Matsumoto et al., (A novel family of heparin-binding growth factors, pleiotrophin and midkine, is expressed in the developing rat cerebral cortex) Developmental Brain Research 79(1994) 229-241.
Nan Zhang et al., (Domain Structure of Pleiotrophin Required for Transformation) vol. 274, No. 19, May 7, 1999, pp. 12959-12962.
Dorothy J. Caughey et al., (Fractionation of polyclonal antibodies to fragments of a neuroreceptor using three increasingly chaotropic solvents) Journal of Chromatography B, 728 (1999) 49-57.
Stephan W. Morris et al., (ALK, the chromosome 2 gene locus altered by the t(2;5) in non-Hodgkin's lymphoma, encodes a novel neutral receptor tyrosine kinase that is highly related to leukocyte tyrosine kinase (LTK) Onogene (1997) 14, 2175-2188.

(Continued)

*Primary Examiner*—Daniel E. Kolker
(74) *Attorney, Agent, or Firm*—Ropes & Gray LLP

(57) ABSTRACT

This invention relates to the discovery that pleiotrophin binds to and activates a pleiotrophin-receptor which is responsible for the events associated with pleiotrophin activity including tumorigenesis, cell proliferation, and cell invasion. By interfering with that association, the cascade of events associated with pleiotrophin activity can be prevented or reversed. Further, by evaluating the effect of different compounds and conditions on the interaction, new drugs and treatments can be identified for use in preventing certain cancers and growth and developmental disorders.

9 Claims, 9 Drawing Sheets

OTHER PUBLICATIONS

Toshinori Iwahara et al., (Molecular characterization of ALK, a receptor tyrosine kinase expressed specifically in the nervous system) Oncogene (1997) 14, 439-449.

Karen Pulford et al., (Detection of Anaplstic Lymphoma Kinase (ALK) and Nucleolar Protein Nucleophosmin (NPM)—ALK Proteins in Normal and Neoplastic Cells With the Monoclonal Antibody ALK1) Blood, vol. No. 4, Feb. 15, 1997. pp. 1394-1404.

A. Aigner, et al., (Identification of a Receptor for the Growth Factor Pleiotrophin, its Signal Transduction and Potential Role in Cancer) Proceedings of AACR; vol. 40, p. 732: Mar. 1999.

Gerald E. Stoica et al., (Identification of Anaplastic Lymphoma Kinase as a Receptor for the Growth Factor Pleiotrophin) vol. 276, No. 20, May 18, 2001, pp. 16772-16779.

James A. Wells, (Additivity of Mutational Effects of Proteins), Biochemistry vol. 29, No. 37, Sep. 18, 1990.

Nobuaki Maeda et al., (A Receptor-like Protein-tyrosine Phosphatase PTP/RPTP B Binds a Herparin-binding Growth Factor Midkine) vol. 274, No. 18, Apr. 30, 1999, pp. 12474-12479.

Temple F. Smith et al., (The challenges of genome sequence annotation or "The devil is in the details") Nature Biotechnology vol. 15, Nov. 1997.

Jeffrey Sknolnick et al., (From genes to protein structure and function: novel applications of computational approaches in the genomic era) Tibtech Jan. 2000, vol. 18, pp. 34-39.

Genetwork (Go hunting in sequence database but watch out for the traps) TIG Oct. 1996, vol. 12, No. 10, pp. 425-427.

Peer Bork (Powers and Pitfalls in Sequence Analysis: The 70% Hurdle) Cold Spring Harbor Laboratory Press (2000) pp. 398-400.

Kung Meng., (Pleiotrophin signals increased tyrosine phosphorylation of B-catenin through inactivation of the intrinsic catalytic activity of the receptor-type protein tyrosine phosphatase B/ζ) PNAS, Mar. 14, 2000, vol. 97, No. 6, pp. 2603-2608.

Gerald E. Stoica., (Identification of Anaplastic Lympoma Kinase as a Receptor for the Growth Factor Pleiotrophin*), Journal of Biological Chemistry, vol. 276, No. 20, May 18, 2001, pp. 16772-16779.

Kenneith M. Merz, Jr. et al., (The Protein Folding Problem and Tertiary Prediction Birkhäuser Boston 1994, Ch 14, pp. 433-506.

Albertoni, M. et al. (Jan. 22, 1998). "Genetic Instability Leads to Loss of Both p53 Alleles in a Human Glioblastoma," *Oncogene* 16(3):321-326.

Bashkin, P. et al., (Feb. 21, 1989). "Basic Fibroblast Growth Factor Binds to Subendothelial Extracellular Matrix and Is Released by Heparitinase and Heparin-Like Molecules," *Biochemistry* 28(4):1737-1743.

Basilico, C. et al., (1992). "The FGF Family of Growth Factors and Oncogenes," *In Advances in Cancer Research* Academic Press, Inc.: San Diego, CA 59:115-165.

Bowers, D.C. et al. (Aug. 1, 2000). "Scatter Factor/Hepatocyte Growth Factor Protects Against Cytotoxic Death in Human Glioblastoma via Phosphatidylinositol 3-Kinase- and AKT-dependent Pathways," *Cancer Res.* 60(15):4277-4283.

Buczek-Thomas, J.A. et al. (1999). "Elastase-Mediated Release of Heparan Sulfate Proteoglycans from Pulmonary Fibroblast Cultures. A Mechanism for Basic Fibroblast Growth Factor (bFGF) Release and Attenuation of bFGF Binding Following Elastase-Induced Injury," *J. Biol. Chem.* 274:25167-25172.

Chauhan, A.K. et al. (Jan. 1993). "Pleiotrophin Transforms NIH 3T3 Cells and Induces Tumors in Nude Mice," *Proc. Natl. Acad. Sci. USA* 90:679-682.

Choudhuri, R. et al. (May 1, 1997). "An Angiogenic Role for the Neurokines Midkine and Pleiotrophin in Tumorigenesis," *Cancer Res.* 57(9):1814-1819.

Czubayko, F. et al. (Aug. 19, 1994). "Ribozyne-Targeting Elucidates a Direct Role of Pleiotrophin in Tumor Growth, "*J. Biol. Chem.* 269(33):21358-21363.

Czubayko, F. et al. (Nov. 11, 1994). "Tumor Growth and Angiogenesis Induced by a Secreted Binding Protein for Fibroblast Growth Factors, " *J. Biol. Chem.* 269(45):28243-28248.

Czubayko, F. et al. (Dec. 1996). "Melanoma Angiogenesis and Metastasis Modulated by Ribozyme Targeting of the Secreted Growth Factor Pleiotrophin," *Proc. Natl. Acad. Sci. USA* 93:14753-14758.

Czubayko, F. et al. (1997). "Adenovirus-Mediated Transduction of Ribozymes Abrogates HER-2/neu and Pleiotrophin Expression and Inhibits Tumor Cell Proliferation," *Gene Therapy* 4:943-949.

Czubayko, F. et al. (Oct. 1997). "Secreted FGF-Binding Protein Can Serve as the Angiogenic Switch in Human Cancer," *Nat. Med.* 3(10):1137-1140.

Dove, A. (Mar. 1999). "Proteomics: Translating Genomics into Products?" *Nat. Biotechnol.* 17:233-236.

Fang, W. et al. (Dec. 25, 1992). "Pleiotrophin Stimulates Fibroblasts and Endothelial and Epithelial Cells and Is Expressed in Human Cancer," *J. Biol. Chem.* 267(36):25889-25897.

Furnari, F.B. et al. (Nov. 1997). "Growth Suppression of Glioma Cells by PTEN Requires a Functional Phosphatase Catalytic Domain," *Proc. Natl. Acad. Sci. USA* 94:12479-12484.

GenBank Accession No. U66559, created on Feb. 24, 1997, located at <http://www.ncbi.nlm.nih.gov> last visited on Mar. 3, 2005, three pages.

Hanahan, D. et al. (Jan. 7, 2000). "The Hallmarks of Cancer," *Cell* 100:57-70.

Holland, E.C. (Jun. 6, 2000). "Glioblastoma Multiforme: The Terminator," *Proc. Natl. Acad. Sci USA* 97(12):6242-6244.

Holland, E.C. et al. (May 2000). "Combined Activation of Ras and Akt in Neural Progenitors Induces Glioblastoma Formation in Mice," *Nat. Genet.* 25:55-57.

James, C.D. et al. (1996). "Molecular Genetics and Molecular Biology Advances in Brain Turmors," *Curr. Opin. Oncol.* 8:188-195.

Khwaja, A. (Sep. 2, 1999). "Akt is More Than Just a Bad Kinase," *Nature* 401:33-34.

Klagsbrun, M. et al. (Oct. 18, 1991). "A Dual Receptor System is Required for Basic Fibroblast Growth Factor Activity," *Cell* 67(2):229-231.

Li, D-M. et al. (Dec. 1998). "PTEN/MMAC1/TEP1 Suppresses the Tumorigenicity and Induces G1 Cell Cycle Arrest in Human Glioblastoma Cells," *Proc. Natl. Acad. Sci. USA* 95:15406-15411.

Li, Y-S. et al. (Dec. 21, 1990). "Cloning and Expression of a Developmentally Regulated Protein That Induces Mitogenic and Neurite Outgrowth Activity," *Science* 250:1690-1694.

Maehama, T. et al. (Apr. 1999). "PTEN: A Tumour Suppressor That Functions as a Phospholipid Phosphatase," *Trends Cell Biol.* 9:125-128.

Merenmies, J. et al. (Oct. 5, 1990). "Molecular Cloning of the 18-kDa Growth-Associated Protein of Developing Brain, " *J. Biol. Chem.* 265(28):16721-16724.

Morris, S.W. et al. (Mar. 4, 1994). "Fusion of a Kinase Gene, *ALK*, to a Nucleolar Protein Gene, *NPM*, in Non-Hodgkin's Lymphoma," *Science* 263:1281-1284.

Morris, S.W. et al. (Jan. 20, 1995). "Fusion of a Kinase Gene, ALK, to a Nucleolar Protein Gene, NPM, in Non-Hodgkin's Lymphoma: Sequence Correction," —Erratum *Science* 267:316-317.

Motegi, A. et al. (2004). "ALK Receptor Tyrosine Kinase Promotes Cell Growth and Neurite Outgrowth," *J. Cell Science* 117:3319-3329.

Nishikawa, R. et al. (Aug. 1994). "A Mutual Epidermal Growth Factor Receptor Common in Human Glioma Confers Enhanced Tumorigenicity," *Proc. Natl. Acad. Sci. USA* 91:7727-7731.

Nistér, M. et al. (Sep. 5, 1991). "Differential Expression of Platelet-Derived Growth Factor Receptors in Human Malignant Glioma Cell Lines," *J. Biol. Chem.* 266(25):16755-16763.

Okada-Ban, M. (Mar. 2000). "Fibroblast Growth Factor-2," *Int. J. Biochem. Cell Biol.* 32(3):263-267.

O'Rourke, D.M. et al. (Apr. 1997). "Trans Receptor Inhibition of Human Glioblastoma Cells by erbB Family Ectodomains," *Proc. Natl. Acad. Sci. USA* 94:3250-3255.

Plate, K.H. et al. (Oct. 29, 1992). "Vascular Endothelial Growth Factor is a Potential Tumor Angiogenesis Factor in Human Gliomas in vivo,"*Nature* 359:845-848.

Powers, C.J. et al. (2000). "Fibroblast Growth Factors, Their Receptors and Signaling," *Endocr. Relat. Cancer* 7(3):165-197.

Schlessinger, J. (Oct. 13, 2000). "Cell Signaling by Receptor Tyrosine Kinases," *Cell* 103:221-225.

Schulte, A.M. et al. (Dec. 1996). "Human Trophoblast and Choriocarcinoma Expression of the Growth Factor Pleiotrophin Attributable to Germ-Line Insertion of an Endogenous Retrovirus," *Proc. Natl. Acad. Sci. USA* 93:14759-14764.

Schulte, A.M. et al (1997). "Pleiotrophin and Related Molecules" Chapter 21 *In Tumor Angiogenesis* Bicknell, R. et al. eds. Oxford University Press: Oxford, UK 1:273-289.

Schulte, A.M. et al. (Jul. 1998). "Structure and Phylogenetic Analysis of an Endogenous Retrovirus Inserted into the Human Growth Factor Gene Pleiotrophin," *J. Virol.* 72(7):6065-6072.

Singer, H.S. et al. (1999). "Mitogenesis in Glioblastoma Multiforme Cell Lines: A Role For NGF and its TrkA Receptors," *Neuro-oncol.* 45(1):1-8.

Souttou, B. et al. (Aug. 1, 1997). "Signal Tranduction Pathways Involved in the Mitogenic Activity of Pleiotrophin. Implication of Mitogen-Activated Protein Kinase and Phosphoinositide 3-Kinase Pathways," *J. Biol. Chem.* 272(31):19588-19593.

Souttou, B. et al. (Oct. 7, 1998). "Relationship Between Serum Concentrations of the Growth Factor Pleiotrophin and Pleiotrophin-Positive Tumors," *J. Natl. Cancer Inst.* 90(19):1468-1473.

Stoica, G.E. et al. (May 18, 2001). "Identification of Anaplastic Lymphoma Kinase as a Receptor for the Growth Factor Pleiotrophin," *J. Biol. Chem.* 276(20):16772-16779.

Wang, S.I. et al. (Oct. 1, 1997). "Somatic Mutations of *PTEN* in Glioblsatoma Multiforme," *Cancer Res.* 57:4183-1486.

Weber, D. et al. (Mar. 1999). "Pleiotrophin (PTN) Serves as an Essential Growth Factor in Pancreatic Cancer," *Proceedings of the 90th Annual Meeting of the American Association for Cancer Research* (Apr. 10-14, 1999) Philadelphia, PA, 40:732, Abstract No. 4834.

Wellstein, A. et al. (Feb. 5, 1992). "A Heparin-Binding Growth Factor Secreted From Breast Cancer Cells Homologous to a Developmentally Regulated Cytokine," *J. Biol. Chem.* 267(4):2582-2587.

Wellstein, A. et al. (1999). "Ribozyme Targeting of Angiogenic Molecules" Chapter 25 *In Antiangiogenic Agents in Cancer Therapy* Teicher, B.A. ed. Humana Press, Inc.: Totowa, NJ. pp. 423-441.

Wen, D. et al. (May 1, 1992). "Neu Differentiation Factor: A Transmembrane Glycoprotein Containing an EGF Domain and an Immunoglobulin Homology Unit," *Cell* 69:559-572.

Wen, S. et al. (Apr. 10, 2001). "PTEN Controls Tumor-Induced Angiogenesis," *Proc. Natl. Acad. Sci. USA* 98(8):4622-4627.

Wu, D. et al. (Sep. 5, 1991). "Characterization and Molecular Cloning of a Putative Binding Protein for Heparin-Binding Growth Factors," *J. Biol. Chem.* 266(25):16778-16785.

Yeh, H.-J. et al. (May 15, 1998). "Upregulation of Pleiotrophin Gene Expression in Developing Microvasculature, Macrophages, and Astrocytes after Acute Ischemic Brain Injury," *J. Neurocsi.* 18(10):3699-3707.

Zhang, N. et al. (Jul. 4, 1997). "Human Breast Cancer Growth Inhibited in Vivo by a Dominant Negative Pleiotrophin Mutant," *J. Biol. Chem.* 272(27):16733-16736.

European Examination Report for European Patent Application No. 01944466.0, mailed on Mar. 22, 2005, 4 pages.

Ledbetter et al., "Agonistic Activity of a CD40-Specific Single-Chaiin Fv Constructed from the Variable Regions of mAb G28-5," *Crit Rev. Immunol.*, 17:427-435 (1997).

MEDCLA586-01, "p.80, Anaplastic Lymphoma Kinase, Clone: 5A4, Mab anti-Human; paraffin, IH/No Wb,".

Santa Cruz Biotechnology catalog pages for sc-6345 and sc-6346.

* cited by examiner

PLEIOTROPHIN GROWTH FACTOR RECEPTOR FOR THE TREATMENT OF PROLIFERATIVE, VASCULAR AND NEUROLOGICAL DISORDERS

REFERENCE TO RELATED APPLICATIONS

This application claims priority to U.S. Provisional application number 60/211,491, filed Jun. 14, 2000.

RIGHTS IN THE INVENTION

This invention was made, in part, with United States government support under a grant from the United States Army, Medical Research Material Command, Breast Cancer Program, and also grant number CA58185, awarded by the National Cancer Institute, Specialized Program or Research Excellence (SPORE), and the United States Government has certain rights in the invention.

BACKGROUND OF THE INVENTION

1. Field of the Invention

The present invention relates to the growth factor pleiotrophin, receptors for pleiotrophin, and fragments of these proteins, as well as nucleic acid sequences that encodes these proteins and protein fragments and antibodies reactive thereto. In particular, the invention relates to compositions and methods related to pleiotrophin and pleiotrophin receptor protein interactions for the treatment, prevention and detection of cell proliferation, vascular, neurological and developmental disorders, and also for the development of new compounds and methods therefor.

2. Description of the Background

Tumors of glial origin, including astrocytomas, oligodendrogliomas and ependymomas, account for almost eighty percent of all primary brain malignancies. Glioblastoma multiforme is both the single most common glial tumor and the most lethal, with a mean survival of only one year despite aggressive treatment (Holland, 2000). While these tumors exhibit multiple genetic alterations, including loss or mutation of the tumor suppressors PTEN (Wang et al., 1997), p53(Albertoni et al., 1998) and INK4a-ARF (James et al., 1996), receptor tyrosine kinase (RTK) signaling seems to play a particularly important role in tumor development and growth. During the development of tumors, a continuos interaction between the malignantly transformed cancer cells and the surrounding stromal cells takes place (Hanahan and Weinberg, 2000). During this cross-talk cancer cells induce other epithelial cells, immune cells, fibroblasts, endothelial cells, etc. to enhance the production of growth factors that will sustain the development of the tumor or, alternatively, to stop producing inhibitory factors that would impede further cancer cell expansion.

Along these lines, tumor cells will secrete growth factors that sustain their own growth by autocrine mechanisms and/or promote the growth of surrounding supportive cells and reduce their inhibitory signals by paracrine mechanisms. Glioblastomas and glioblastoma cell lines have been shown to overexpress the tyrosine kinase receptors for epidermal growth factor (EGF) (Nishikawa 1994), platelet-derived growth factor (PDGF) (Nister et al., 1991), hepatocyte growth factor (HGF) (Bowers et al., 2000), nerve growth factor (NGF) (Singer et al., 1999) and vascular endothelial growth factor (VEGF) (Holland et al., 2000). In addition, these tumors frequently overexpress the ligands for these RTKs, indicating a potential role for autocrine RTK signaling in glioblastoma growth. The importance of RTK signaling is also supported by the finding that the combined activation of two downstream targets of RTK signaling, Ras and Akt, in neural progenitor cells induces glioblastoma-like tumors in mice (Holland et al., 2000).

SUMMARY OF THE INVENTION

The present invention overcomes the problems and disadvantages associated with current strategies and designs and provides new diagnostic, therapeutic and research tools, and methods relating to interactions between pleiotrophin and pleiotrophin receptors for the treatment and prevention of disorders. In particular, the invention relates to compositions and methods comprising pleiotrophin and pleiotrophin-receptor proteins, active fragments thereof and antibodies thereto, for stimulating or inhibiting cell proliferation.

One embodiment of the invention is directed to isolated polypeptide complexes comprising a pleiotrophin protein and a pleiotrophin-receptor protein. Pleiotrophin protein includes, but is not limited to, PTN, miple, midkine, recombinant pleiotrophin and combinations thereof. Pleiotrophin-receptor protein includes, but is not limited to, ALK, LTK, recombinant pleiotrophin-receptor protein and combinations thereof. Complexes may be physically bound to each other or unbound, and comprise whole proteins, protein fragments, recombinant proteins or fragments, synthetic proteins or fragments, proteins or fragment of human or non-human origin, or combinations thereof. Pleiotrophin-receptor protein fragments may lack a signal transduction activity such as, for example, tyrosine kinase activity, and preferably comprise one or more, but not all portions of a full-length pleiotrophin receptor protein. The various portions of the pleiotrophin-receptor protein comprise an extracellular domain, an intracellular domain, a pleiotrophin binding site, a growth factor binding site, a mitogenic factor binding site, a tyrosine kinase, an antigenic domain, a heparin binding site, a glycosylated domain, a non-glycosylated domain, a signaling domain, a functional domain, a conserved domain, a transmembrane domain, and combinations thereof.

Another embodiment of the invention is directed to recombinant polypeptides comprising one or more, but not all regions of a full-length pleiotrophin receptor protein. The one or more regions include, but are not limited to an extracellular domain, an intracellular domain, a pleiotrophin binding site, a growth factor binding site, a mitogenic factor binding site, a tyrosine kinase, an antigenic domain, a heparin binding site, a glycosylated domain, a non-glycosylated domain, a signaling domain, a functional domain, a conserved domain, a transmembrane domain, and combinations thereof. Polypeptides are preferably antigenic and may have anti-angiogenic activity, induce apoptosis, or possess anti-motogenic, anti-mitogenic, cell proliferative or anti-cell proliferative activity.

Another embodiment of the invention is directed to nucleic acids that encode polypeptides of the invention. For example, nucleic acid may encode functionally or antigenically active polypeptides. Further, nucleic acids may be contained in vectors which may be further maintained in a host cell or organism.

Another embodiment of the invention is directed to compositions comprising polypeptides of the invention. Preferably, these polypeptides contain a pleiotrophin-binding site, and may be recombinant, synthetic or peptido-mimetics. Recombinant polypeptides may comprise one or more, but not all regions of a full-length pleiotrophin protein. Regions that may be included are a pleiotrophin receptor binding portion, which binds, but does not activate a pleiotrophin-receptor protein. Further embodiments include nucleic acids that encode these polypeptides, which may encode functionally or antigenically active polypeptides, vectors that contain these nucleic acids, and compositions comprising the polypeptides, which may further contain a pharmaceutically acceptable carrier such as, for example, water, oils, alcohols, salts, fatty acids, saccharides, polysaccharides and combinations thereof.

Another embodiment of the invention is directed to antibodies that are reactive against a pleiotrophin protein such as, for example, PTN, and also antibodies that are specifically reactive against pleiotrophin-receptor proteins such as, for example, ALK. Preferably, antibodies are reactive against the interacting sites of the pleiotrophin protein and the pleiotrophin-receptor protein, and may be of any isotype or fragment including, but not limited to, IgG, IgM, Fab fragments, Fv fragments, recombinant antibodies and humanized antibodies. Preferably the antibody is a monoclonal antibody and, thus, the invention is further directed to hybridomas that produce such monoclonal antibodies. A pleiotrophin binding site of the pleiotrophin-receptor protein ALK is preferably between amino acid sequence positions 368 and 447, with the actual contact site between amino acid sequence positions 391 and 401. Antibodies of the invention may block or stimulate activation of the pleiotrophin-receptor protein.

Another embodiment of the invention is directed to kits comprising a pleiotrophin-binding region of a pleiotrophin-receptor protein and a pleiotrophin-receptor binding region of a pleiotrophin protein, for screening substances for an ability to block interaction between pleiotrophin and pleiotrophin receptor. The pleiotrophin-binding region preferably comprises amino acid positions 391-401 of ALK, and substances which can be evaluated for their ability to interfere with interaction include, but are not limited to, antibodies, additional pleiotrophin proteins, additional pleiotrophin-receptor proteins, drugs, anti-angiogenic substances, anti-proliferative substances, anti-motogenic substances, anti-metastatic substances, apoptotic substances, anti-tumorigenic substances, anti-neoplastic substances, biologically active substances and combinations thereof.

Another embodiment of the invention is directed to methods for evaluating an activity of a substance to block interaction between pleiotrophin and pleiotrophin receptors comprising incubating an amount of the substance with at least interacting portions of a pleiotrophin protein and a pleiotrophin receptor protein, determining a first measure of interaction between the interacting portions, comparing the first measure of interaction with a second measure of interaction determined with a different amount of the substance, and evaluating the activity of the substance. Incubating may comprises contacting the substance with the interacting portions for a predetermined period of time and at a predetermined temperature. Preferably the predetermined period of time is between one second and ten minutes, but may be longer or shorter as desired, and the predetermined temperature is between 4° C. and 37° C., but may be warmer or cooler, as desired. The amount of substance to be tested is preferably a physiologically effective amount, but may be any amount including, but not limited to, no substance, ten percent of a physiologically effective amount, twenty percent of a physiologically effective amount, fifty percent of a physiologically effective amount, a physiologically effective amount, two times a physiologically effective amount and ten times a physiologically effective amount. Substance that can be evaluated include, but are not limited to, antibodies, additional pleiotrophin proteins, additional pleiotrophin-receptor proteins, drugs, anti-angiogenic substances, anti-proliferative and proliferative substances, anti-motogenic and motogenic substances, anti-metastatic substances, apoptotic substances, anti-tumorigenic substances, anti-neoplastic substances, biologically active substances and combinations thereof. Further, activities that can be tested include, but are not limited to, anti-angiogenic activity, anti-proliferative and proliferative activity, anti-motogenic and motogenic activity, anti-metastatic activity, apoptotic activity, anti-tumorigenic activity, anti-neoplastic activity, and combinations thereof. A further embodiment includes a method for evaluating an activity of a substance comprising incubating the substance with at least interacting portions of a pleiotrophin protein and a pleiotrophin receptor protein for a first period of time, determining a first measure of interaction between the interacting portions, incubating the substance with the at least the interacting portions for a second period of time, determining a second measure of interaction between the interacting portions, comparing the first measure of interaction with the second measure of interaction, and evaluating the activity of the substance.

Another embodiment of the invention is directed to kits for the detection of cell proliferative diseases such as, for example, cancer and heart disease. Kits comprise all or characteristic portions of pleiotrophin and/or pleiotrophin receptor proteins, or antibodies to these proteins and/or polypeptides.

Another embodiment of the invention is directed to methods for treating a patient, preferably a human, comprising administering to said patient a therapeutically effective dose of a composition comprising a pleiotrophin-receptor protein or fragment thereof. Preferably, administering comprises direct injection of the composition, and the therapeutically effective dose is that amount which will bind to at least half of free pleiotrophin of said patient. Fragments preferably comprise a pleiotrophin-binding portion of the pleiotrophin-receptor protein. Preferably, treatment stimulates a cell proliferation such as creation and growth of blood vessels, or prevents a cell proliferation such as a tumor or a metastasis. A further embodiment of the invention is directed to methods for blocking or stimulating tyrosine kinase activity, and thereby stimulating an anti-neoplastic effect, by interfering with the binding of pleiotrophin with pleiotrophin receptor. Interference with binding and/or interaction can be performed by administering to patients compositions containing modifications and/or derivatives of pleiotrophin, antibodies to pleiotrophin-binding sites or other compounds that block receptor activation. Compositions of the invention may be administered in a therapeutically safe and effective dose to humans and other mammals in the form of pills, tablets, powder, liquid or combinations thereof.

Another embodiment of the invention is directed to compositions and methods comprising pleiotrophin, pleiotrophin-receptor, and modifications and derivatives of either that are useful as pharmaceuticals in the treatment or prophylaxis of diseases such as cell proliferative disorders including cancer and heart disease. Compositions may be useful in therapy, prophylaxis, diagnosis, or as research tools, and may further comprise pharmaceutically acceptable carriers for use in the treatment or prevention of diseases and disorders. A further embodiment is directed to compositions comprising nucleic acid sequences that contain the anti-sense of pleiotrophin or pleiotrophin-receptor genes or representative portions thereof. Sequences may be useful in compositions for the treatment of breast and other neoplastic disorders by reducing or shutting down pleiotrophin receptor expression in cells.

Other embodiments and advantages of the invention are set forth in part in the description which follows, and in part, will be obvious from this description, or may be learned from the practice of the invention.

DESCRIPTION OF THE INVENTION

Figure 1:
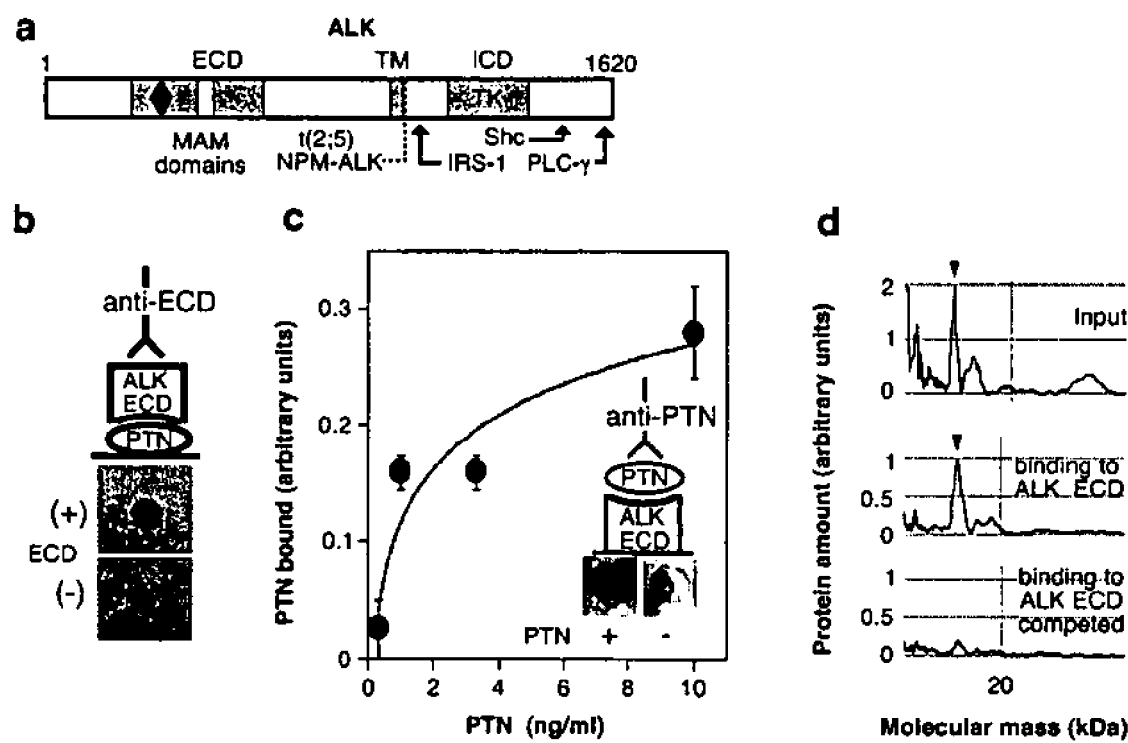
FIG. 1 (a) Schematic of ALK gene showing factor binding sites. (b) Binding of the PTN to recombinant ECD of ALK. (c) SELDI analysis of PTN-ligand binding. (d) SELDI analysis of conditioned media, initial PTN binding to ECD, and completed PTN binding to ECD.

As embodied and broadly described herein, the present invention is directed to nucleic acid sequences encoding pleiotrophin and pleiotrophin-receptor proteins, to complexes of these proteins and protein fragments, to pharmaceutical compositions comprising proteins, complexes and fragments thereof, to antibodies to these proteins and polypeptides, to kits and methods that relate to interaction between pleiotrophin and pleiotrophin receptor, and to compositions and methods for the treatment, prevention and detection of disease and, in particular, neoplastic disease in patients.

Pleiotrophin is a heparin-binding growth factor that has been implicated in tumor growth, cellular invasion of tissues (i.e. motogenic), angiogenesis and metastasis. As used herein, the term pleiotrophin refers to a family of proteins that bind to a pleiotrophin receptor and share a similar conserved sequence. Members of this family include isoforms thereof, and have been identified in the human (PTN; midkine), the rat, the mouse (PTN, midkine), the chicken, the fruit fly Drosophila (miple), and many other species, and is believed present in most all eukaryotic species including yeast and insects. Pleiotrophin is expressed in a developmentally regulated manner in rat brain (Li et al., 1990; Merenmies and Rauvala, 1990), and also promotes neurite outgrowth activity. This growth factor is highly expressed in the developing nervous system, but down-regulated in adults. Further, pleiotrophin is secreted by human cancer cell lines (Wellstein et al., 1992), and has mitogenic activity on fibroblast, epithelial and endothelial cells and, thus, contributes to the metastatic phenotype as a tumor growth factor and angiogenic factor (Schulte and Wellstein, 1997). Serum samples from cancer patients contain elevated levels of pleiotrophin that can stimulate cells both in an autocrine as well as a paracrine manner (Schulte and Wellstein, 1998; Souttou et al., 1998). In addition, pleiotrophin targeting by ribozymes (Czubayko et al., 1997a) or by transfection of mutant pleiotrophin cDNA that leads to the formation of inactive dimers (Zhang et al., 1997), inhibited human cancer cell growth in animal models.

Relative to normal brain, pleiotrophin expression is elevated following acute ischemic injury (Yeh et al., 1998), and also in tumors (Schulte et al., 1997), thus implicating pleiotrophin as a tumor growth factor insofar as the reactivation of a developmentally-regulated signaling pathway may provide a tumor with a powerful growth signal. And, in fact, pleiotrophin expression induces tumor growth and metastasis of NIH3T3 cells (Chauhan et al., 1993), and has a rate-limiting role both as an angiogenic factor (Choudhuri et al., 1993) and a tumor growth factor for different tumors including melanoma and choriocarcinoma (Czubayko et al., 1994; Czubayko et al., 1996; Schulte et al., 1996; Schulte et al., 1997). In addition, pleiotrophin activates both the Ras-MAPK and the PI3K-Akt signaling axes (Souttou et al., 1997), both pathways implicated in glial tumorigenesis (Holland et al., 2000). In view of these functions, dysregulation of pleiotrophin would have substantial implications for the treatment of diseases such as neurodegenerative disease and cell proliferative disorders such as cancer.

It was surprisingly discovered that, ALK, an orphan RTK, is a cell receptor for pleiotrophin in humans. As a previously unknown target for the ligand, this receptor provides a mechanism to regulate physiological functions attributed to pleiotrophin, which include, but are not limited to, prevention and treatment of cell proliferative disorders such as cancer, induction of neurite outgrowth, maintenance of neuronal function, maintenance of developmental regulation, promotion of cell proliferation for wound healing and, in particular, endothelial cell proliferation such as, for example, vessel and microvessel growth and formation in cardiac tissues, in both central and peripheral neural tissues, and any endothelial cells of the body. The pleiotrophin activity, ALK tyrosine kinase, was originally identified as a fusion protein with nucleophosmin (npm/ALK) due to a t(2;5) translocation (Morris et al., 1994). This fusion results in constitutive activation of the intracellular ALK kinase and was shown to induce anaplastic lymphoma. The full-length ALK receptor has been shown to be highly expressed in the developing nervous system and down-regulated postnatally (Iwahara et al., 1997), very similar to the expression profile of its ligand, pleiotrophin. As shown in Table 1, ALK expression (or the lack thereof) correlated with the growth effect of pleiotrophin on cells tested. It has also been surprisingly discovered that this tyrosine kinase receptor is over expressed in human glioblastoma and is rate-limiting for the growth of a xenograft model of glioblastoma. The term pleiotrophin-receptor protein, refers to a family of proteins, including isoforms, that are involved in pleiotrophin stimulation or signaling. Members of this Members of this family have been identified in humans, rats, mice, chickens, Drosophila, and many other species, and is believed present in most all eukaryotic species including yeast and insects. Although all have the common feature in that they are involved in pleiotrophin stimulation, some, like ALK (mouse and human), actually bind to pleiotrophin while others, like LTK (Drosophila), act as co-signaling proteins or co-receptor proteins that are involved in the down-stream signaling (i.e. signal transduction) that results from pleiotrophin binding.

Accordingly, one embodiment of the invention is directed to isolated complexes comprising pleiotrophin protein and pleiotrophin-receptor protein. These complexes may comprise all or specific portions of pleiotrophin and/or pleiotrophin-receptor proteins. Complexes may be physically bound (covalently or non-covalently) or unbound. The human pleiotrophin receptor, ALK, is composed of three principal regions, an extracellular domain (ECD), a transmembrane region (TM), and an intracellular domain (ICD) (see FIG. 1a). Within the ECD is the pleiotrophin-binding site (amino acids 368-447 with actual contacts at amino acids 391-401) which, upon binding with pleiotrophin, induces pleiotrophin-associated functions including cell proliferation such as tumor growth, endothelial cell growth and neural cell growth, activation of Ras-related activities, cellular invasion (motogenic activities) such as metastasis, angiogenic activities, and developmental regulation to name a few. Within the ECD are also the MAM domains, typical signature sequence patters for ECDs. MAM domains are also found in Drosophila ALK protein which contains the PTN binding site and has an overall 42% similarity with the human ALK protein. In contrast, LTK, the closest homolog of ALK is a 100-kDa transmembrane protein with a short ECD that lacks 60% of the N-terminal portion of the ALK ECD and the PTN binding domain. The MAM domains of ALK, one of which encompasses the pleiotrophin-binding site, are found in the ECDs of a diverse family of transmembrane proteins (Proite Database PDOC 00604). The ICD contains the tyrosine kinase activity and the translocation site in the juxtamembrane region for fusion with nucleophosmin (t(2,5) NPM-ALK). The ICD also contain consensus binding sites for insulin receptor substrate-1 (IRS-1), and binding sites for the factors Shc and PLC-gamma. The protein is also believed to be glycosylated and contain one or more heparin-binding sites. Pleiotrophin and pleiotrophin-receptor proteins such as human and mouse ALK, and Drosophila LTK have been cloned and their gene sequences may be recombined to express only one or more of the nucleic acid or amino acid domains (e.g. exons, introns, conserved amino acid or nucleic acid regions, open reading frames in any of the three possible reading frames, binding sites for pleiotrophin, mitogenic factors, growth factors, motogenic factors, insulin and heparin, signaling domains, glycosylated and non-glycosylated regions, functional domains, co-receptors, co-signaling factors, and consensus sequences of the pleiotrophin-receptor proteins). For example, factors containing only a pleiotrophin-binding portion and not a signaling or tyrosine kinase portion may be useful to bind pleiotrophin and, thereby, effectively remove pleiotrophin stimulation from a disease pathway. These blocking or interfering peptides may be free in solution (e.g. aqueous or non-aqueous such as oil-based), or contain a transmembrane portion (of ALK or another appropriate portion) to fix such recombinant molecules in cell or vesicle walls to more effectively or efficiently bind pleiotrophin. Alternatively, the tyrosine kinase activity or other signaling activity may be engineered out of pleiotrophin-receptor proteins such that pleiotrophin binding would not have the undesirable effect such as a mitogenic, motogenic or cell proliferative effect, but would have one or more positive activities such as induction of apoptosis, or an anti-proliferative or anti-metastatic effects. Further still, one or more other binding sites may be engineered into the pleiotrophin receptor protein such that pleiotrophin binding would induce a cascade of beneficial functions to a host to fight disease or maintain proper development. Homologs and derivatives of these protein fragments may be created by those of ordinary skill in the art. Homologs are peptides that are functional equivalents to the peptides of the invention, but contain differences such as, for example, one or more of the amino acid substitutions including, but not limited to, one or more conservative amino acid substitutions. Proteins and protein fragments including isoforms, recombinant proteins, homologs, derivatives (e.g. modified proteins and homologs such as glycosylation changes) and bound complexes may be isolated from one or more other components, or purified to homogeneity or near homogeneity, as desired.

Procedures to isolate and purify pleiotrophin and pleiotrophin-receptor protein, protein fragments, recombinant proteins and complexes thereof are well known to those of ordinary skill in the art. Alternatively, proteins and polypeptides of the invention can be recombinantly or synthetically produced. Recombinant polypeptides can be created by manipulating the nucleic acid sequences of the invention removing undesired portion and/or adding other desired portions. Synthetic polypeptides of the invention can be created by replacing amino acid sequences of the polypeptides with non-natural amino acids or substituting the natural L forms of one or more amino acids to D-amino acids. In this way, polypeptides of the invention can be created that are resistant to proteases that may be found in a body. Further, peptido-mimetic polypeptides can be created which mimic the three-dimensional structure of the polypeptide, or portion thereof, for purposes of evaluating structure-function relationships. All these procedures are well-known to those of ordinary skill in the art.

Another embodiment of the invention is directed to nucleic acids that comprises all or one or more portions of the sequence of a pleiotrophin receptor, to peptides derived from these sequences, and to sequences complementary thereto. The nucleic acid sequence that encodes the pleiotrophin receptor, ALK, can be found in GenBank at accession number U66559, which provides a human ALK nucleic acid sequence (SEQ ID No:1) and its corresponding CDS (SEQ ID NO:2). Nucleic acids of the invention may be single-stranded or double-stranded and composed of DNA, RNA or PNA, or another appropriate nucleic acid, polypeptide or functionally similar backbone structure. Single stranded nucleic acids may be in the form of a sense strand or an anti-sense strand. Further, receptor genes of the invention may be derived from other mammals besides humans (using identification and isolation procedures and techniques that are well known to those of ordinary skill in the art) such as, for example, mice, rats or any rodent, mammals such as cattle, sheep, goats, pigs, horses, canines and felines, and most any other animal. Receptor genes of the invention include other nucleic acid sequences that may be identified, using techniques and procedures well known to those of ordinary skill in the art, that are found in insects (Drosophila), plants, yeast and other eukaryotic organisms.

Nucleic acids according to the invention include isolated (e.g. semi-purified and purified to homogeneity) and recombinant nucleic acid sequences comprising all or one or more active fragments of the pleiotrophin-receptor polypeptide. Nucleic acids containing conserved regions of sequences and nucleic acids encoding open reading frames and conserved domains within open reading frames are typically sufficient to represent or contain identifiable portions of pleiotrophin receptor such as functional and antigenic portions. Nucleic acids may comprise additional sequences such as pleiotrophin receptor-specific promoters, activator and repressor sites, and enhancers for modulation of expression of sense or antisense messages, recombination sequences for gene targeting, selectable markers for transfections, or replication origins for passage in a host such as bacteria or any prokaryotic cells, virus, eukaryotic cells or yeast. Thus, the invention includes recombinant cells containing nucleic acids of the invention. A further embodiment of the invention includes pleiotrophin receptor-specific promoters which modulation transcription of pleiotrophin receptor in normal, pre-malignant and malignant cell. These promoters can be functionally coupled to anti-neoplastic genes to diagnose, identify, treat or prevent cell proliferative disorders such as, for example, tumors, breast carcinoma, prostate cancer, and metastatic disease, development disorders and neurological disorders, and also endothelial disorders in which cell proliferation is desired. Nucleic acids may be packaged in a viral vector such as, for example, a retroviral, a vaccinia or an adenoviral vector. In one embodiment, the sequence may be part of a homologous recombination vector designed to recombine with another sequence. The invention further includes vectors comprising the nucleic acid sequences of the invention, polypeptides expressed by these vectors, and recombinant cells comprising these vectors.

Nucleic acids and polypeptides or proteins according to the invention may be used as a diagnostic or therapeutic tool in the detection, treatment or prevention of diseases, such as neoplastic disorders (e.g. malignant tumors, metastatic disease), developmental disorders, neuronal cell disorders, and cell or tissue growth disorders. For example, one embodiment of the invention is directed to diagnostic aids or kits for the detection of disorders in a patient. Detection kits may comprise pleiotrophin-receptor nucleic acid sequences or pleiotrophin-receptor polypeptides whose presence or absence in the sample would be indicative of the presence of a disease such as, for example, breast cancer or a metastasis. As shown in Table 1, there is a clear correlation of expression of ALK with PTN response. Further, as there was no detectable ALK mRNA in hematopoietic cells, side effects attributable to therapeutics of the invention, or developed with the invention, are expected to be minimal. Samples which can be analyzed include samples of biological fluids (e.g. blood, plasma, interstitial fluid, urine, cerebrospinal fluid) and samples of biological tissue (e.g. surgical biopsy). Another embodiment is directed to compositions and method for the treatment of patients that induce cell proliferation and, in particular, endothelial cell proliferation. Endothelial cells are found throughout the body and in most every organ including the brain, heart and peripheral nervous system. After an ischemic attack or any restriction of blood flow or circulation, there is typically damage to effected regions or organs of the body such as, for example, the heart, retina or a limb (such as occurs in diabetics). Compositions of the invention can be used to stimulate endothelial cell proliferation and specifically the proliferation and generation of new blood vessels to effected areas.

Another embodiment of the invention is directed to antibodies specifically reactive against polypeptides and proteins and fragments thereof of the invention. Antibodies may be polyclonal or monoclonal of any isotype (e.g. IgA, IgD, IgE, IgG1, IgG2a, IgG2b, or IgM), or antibody fragments (e.g. Fab, Fv), humanized antibodies, or recombinant or synthetic antibodies (e.g. variable region fragments). Further, the invention comprises hybridomas that express antibodies specifically reactive against proteins and polypeptides of the invention. Preferably, antibodies are specifically reactive against the interacting portions of pleiotrophin and the pleiotrophin receptor. Antibodies have been created which block binding between the two proteins. These antibodies were created to be reactive against amino acid sequence 368-447 of the receptor protein, which is believed to be the region directly involved in protein-protein interaction. Antibodies that interfere and negatively effect pleiotrophin-receptor protein activation as well as antibodies that positively stimulate pleiotrophin-receptor protein activation have been developed. Both are useful in methods of the invention. For example, such antibodies (i.e. antibodies that interfere with pleiotrophin binding and/or interact with receptor at the pleiotrophin-binding site) that negatively stimulate the receptor protein are useful as therapeutics in the treatment of tumors and metastatic disease. Such antibodies that positively stimulate the receptor protein are also useful to induce cell proliferation when, for example, the proliferation of blood vessels and microvessels is desired after a stroke or heart attack, or to prevent limb, organ or tissue degeneration in diabetics.

Another embodiment of the invention is directed to kits and methods which can be used to screen various substances for the ability to effect pleiotrophin-pleiotrophin receptor interaction and/or pleiotrophin receptor signaling. Kits may comprise he interacting portions of the pleiotrophin and pleiotrophin receptor proteins. Preferably, the portion of the pleiotrophin-receptor protein comprises the pleiotrophin-binding region such as, amino acids 368-447 or 391-401 of ALK. Basically, substances to be examined are incubated in the kits with the interacting portions. Incubations may be for a predetermine time and at a pre-determined temperature. Preferably, times are between one second and ten hours, preferably between one minute and one hour, and longer for incubations with cells such as between one and thirty days, preferably between two and ten days, but may be longer or shorter for each as desired or as the materials require. Temperatures are preferably between 4°C. and 37 °C., but may be warmer or cooler as desired. More preferably, incubations are conducted at room temperatures (e.g. between 19°C. and 25°C.). Using the peptides of the invention, incubations can be varied to evaluate the effects of exposure time on the interaction of the substance. This evaluation is not possible using proteins that are constitutively turned on (i.e. induce signaling effects as if continually bound with pleiotrophin). Substances that can be evaluated include most any substance such as, for example, antibodies, different pleiotrophin proteins, different pleiotrophin-receptor proteins, drugs, anti-angiogenic substances, anti-proliferative and proliferative substances, anti-motogenic and motogenic substances, anti-metastatic substances, apoptotic substances, anti-tumorigenic substances, anti-neoplastic substances, biologically active substances and combinations thereof. Activities that can be examined or tested include, for example, anti-angiogenic activity, anti-proliferative activity, anti-motogenic activity, anti-metastatic activity, apoptotic activity, anti-tumorigenic activity, anti-neoplastic activity, and combinations thereof.

Another embodiment of the invention is directed to a method for treating a disorder comprising administering a therapeutically effective amount of a composition comprising pleiotrophin-receptor proteins, fragments or ligands of these proteins and fragments. Such compositions may be anti-angiogenic, induce apoptosis, induce cell proliferation (e.g. endothelial and blood vessel growth), and/or stimulate a cell or humoral response. For example, in cell growth disorders such as breast cancer and other neoplasias, cytokine expression may be improperly turned off (e.g. methylated) in malignant or pre-malignant cells. As such, these gene products may also be useful as a diagnostic for malignancy. A therapeutically effective dose in a mammal is that amount of protein or protein fragment that will bind at least half, and preferably at least 70% and more preferably at least 90% of the available pleiotrophin of a patient. Alternatively, compositions of the invention may be useful in, for example, neurological or developmental disorders to turn on genes whose activity may be improperly reduced or turned off. Further, polypeptides of the invention may induce apoptosis and are useful as therapeutics to treat and prevent neoplasia such as, for example, tumors, metastasis and any uncontrolled cell growth. A further embodiment of the invention comprises the pleiotrophin-receptor promoters which may be differentially modulated and thereby regulate expression of a desired gene. Alternatively, pleiotrophin-receptor protein, or effective portions thereof, may be useful to treat patients by binding available pleiotrophin in a system and thereby preventing pleiotrophin stimulation.

The peptide, polypeptide, protein or fragment thereof, or ligand thereto, may be administered by injection, orally, pulmonary absorption, topical application or delayed release, as desired. Although parenteral administration would be preferred, administration of pleiotrophin receptor would preferably be by injection directly to the tumor, tissue and/or cells to be treated as unprotected proteins would be broken down in the gut or after prolonged exposure to a patient system. The composition may further comprise a pharmaceutically acceptable carrier such as water, alcohols, salts, oils, glycerols, fatty acids, starches, saccharides, polysaccharides or combinations thereof. More than one carrier may be used together to create a pharmaceutical with desirable properties such as delayed release, protection from the harsh gut environment and the like. A further embodiment of the invention comprises vaccines for the treatment and/or prevention of cell proliferative disorders such as neoplastic disease and also diabetes (where growth of blood vessels in the body is desired). Vaccines may comprise antibodies reactive against polypeptides and/or polypeptide fragments of the invention, and the polypeptides and/or fragments themselves. Vaccines comprise therapeutically effective doses of the therapeutic agent, which may be the polypeptide or polypeptide fragment, or an antibody or collection of antibodies which bind or are otherwise reactive thereto.

Another embodiment of the invention is directed to nucleic acids therapies derived or based on the sequence of pleiotrophin receptor (e.g. ALK), useful in diagnosis and in diagnostic kits. Therapy may involve using the sequences, or effective parts thereof, in gene therapy, including gene ablation, gene expression and gene suppression, such as anti-sense suppression. Diagnosis may involve genotypic analysis of samples to determine the existence and expression levels of the genes. Nucleic acids of the present invention may be used in various treatment and research modalities, including gene replacement, gene targeting, anti-sense inhibition, anti-sense blocking, genetic ablation and gene silencing. Gene replacement involves replacing a copy of a defective gene with another copy by homologous recombination. Gene targeting involves the disruption of a cellular copy of a gene by homologous recombination. Gene targeting refers to a process of introducing a nucleic acid construct into a cell to specifically recombine with a target gene in the cell. The nucleic acid construct inactivates the gene after targeting. Inactivation may be by introduction of termination codons into a coding region or introduction of a repression site into a regulatory sequence. Anti-sense inhibition exploits the specificity of hybridization reactions between two complementary nucleic acid chains to suppress gene expression. If a cloned gene is engineered so that only the opposite DNA strand is transcribed, the resultant RNA may hybridize to the sense RNA and inhibit gene expression. Anti-sense blocking refers to the incorporation into a cell of expression sequences which direct the synthesis of anti-sense RNA to block expression of a target gene. Anti-sense RNA hybridizes to the mRNA of the target gene to inhibit expression. Genetic ablation (gene knockout) refers to one process of silencing a gene in a cell. Genetic ablation (gene knockout) may be performed after a cell is selected for use or by selecting a cell already comprising a genotype with the proper genetic ablation. Ablation of the gene encoding pleiotrophin-receptor protein, for example by pre-transcriptional inhibition (such as homologous recombination with endogenous recessive oncogenes) or post transcriptional inhibition (such as the expression of anti-sense oncogenes to suppress translation) may be useful. Gene silencing is performed by transfecting cells with nucleic acids which cause genetic ablation or by anti-sense suppression. The silencing process may include processes such as gene targeting or anti-sense blocking.

Another embodiment of the invention is directed to methods of blocking of pleiotrophin-mediated activities. Blocking involves interfering with pleiotrophin binding and/or activation of the pleiotrophin receptor and, as a consequence, reducing or eliminating pleiotrophin-mediated activities such as, for example, tyrosine kinase activity of the receptor protein. Blocking receptor protein activity can play a significant role in development and a therapeutic role in disease processes by, for example, inducing for example, apoptosis, anti-angiogenesis, maintaining the regulation of development, maintaining neuronal function, preventing the activation of Ras and other oncogene pathways, reducing invasion by transformed cells of tissues and organs, preventing or reducing metastatic induction, and depriving transformed cells and tumors of access to growth factors, angiogenic factors, mitogenic factors. Blocking may be performed by administering proteins or protein fragments of the invention which retain the ability to bind pleiotrophin, but not activate pleiotrophin-receptor pathways, or prevent tyrosine kinase activity of the pleiotrophin receptor. Suitable blocking molecules include recombinant pleiotrophin-receptor proteins of the invention, analogs of pleiotrophin-receptor proteins that retain pleiotrophin binding ability, but lack or have a modified tyrosine kinase activity, a transmembrane portion, insulin binding sites, transcription or translation controlling sequences, or any combination thereof. It is especially important to note that blocking may both inactivate the receptor or activate the receptor protein. Stimulation of the receptor is desired in instances where pleiotrophin activities are desired such as, for example, with non-cancerous endothelial cell proliferation for the development of blood vessels and surrounding tissues after ischemic attack.

The following examples illustrate embodiments of the invention, but should not be view as limiting the scope of the invention.

EXAMPLES

Example 1

Identification of the PTN Receptor.

Signal transduction studies regarding the effects of PTN were impeded by the lack of a receptor involved. Recently, it was discovered that a receptor for PTN by phage display technique (FIG. 1). PTN receptor fragments were identified using a phage display library of human fetal brain cDNAs. An M13 phage-display library of human fetal brain cDNA (Easy-MATCH Phage Display) was obtained from Clontech. The human cDNA fragments are located downstream of the phage gene III leader sequence in order to generate gene III fusion proteins that are exposed on the phage surface. Phage containing candidate PTN receptor cDNA fragments as inserts were selected by repeated panning of the library with purified PTN (~1 µg per well) that had been immobilized in the wells of a 96-well plate. Panning of selected clones against FGF-2 was used as a negative control. Several rounds of panning against purified, biologically active PTN resulted in the isolation of two distinct phages that bound to PTN. Shown in FIG. 1(a) is the general scheme for panning of a human fetal brain cDNA phage-display library against immobilized PTN protein. One of the selected clones contained an insert homologous to a sequence in the extracellular domain (ECD) of the orphan receptor ALK (GenBank number U66559). The regions and percent homology of the ALK protein with other tyrosine kinase receptors are indicated. NP-1=neuropilin-½, LTK=leukocyte tyrosine kinase, IGF1-R=insulin-like growth factor-1 receptor, IR=insulin receptor t(2,5) NPM ALK=nucleophosmin-ALK fusion protein. One of these encoded for a peptide sequence homologous to a region in the ECD of an orphan receptor tyrosine kinase, ALK (Stoica et al., 2001). Homology of the amino acid sequence in one of the phage inserts with a sequence stretch in the extracellular domain (ECD) of the Anaplastic Lymphoma Kinase (ALK) transmembrane receptor suggested that PTN could be a ligand for this orphan receptor with an apparent molecular mass of 200 to 220 kDa. As indicated in FIG. 1a, the ligand binding domain recognized by the phage display is N-terminal of regions of homology between ALK and the leukocyte tyrosine kinase (LTK)—a close relative of ALK- and is not shared with any other protein in the data base (Stoica et al., 2001). ALK was discovered in anaplastic lymphoma and was found to be constitutively activated in this cancer due to a t(2,5) chromosomal translocation and a resulting fusion between the nucleophosmin protein and the intracytoplasmic kinase domain of ALK (Morris et al., 1994).

Example 2

Cell-free Binding Assays With Nitrocellulose Membrane-immobilized Proteins

To prove that the PTN ligand indeed binds to the ALK receptor, both cell-free and whole-cell assays were used. For the initial cell-free assays, the PTN protein or the recombinantly produced extracellular domain (ECD) of ALK or an aliquot of fetal calf serum were immobilized by spotting onto nitrocellulose membranes (FIG. 1b). Briefly, PTN purified from the culture supernatant of cells transfected with the human PTN cDNA (approximately 5 ng of biologically active protein in 5 µl) (Souttou et al., 1997) or the ECD of PTNR produced as an Fc fusion protein in CHO cells as described (Wen et al., 1992) (approximately 7.5 ng in 10 µl), or fetal bovine serum as a negative control (2 µl) were immobilized by spotting onto a nitrocellulose membrane. Nonspecific binding sites were blocked by incubation of the membranes with 5% (w/v) skim milk in Tris-buffered saline containing 0.1% (v/v) Tween-20 (TBST). Membranes were then incubated for 2 hours at room temperature with PTN (in TBST), PTNR ECD protein (2 µg/ml in TBST), or TBST alone (negative control) as appropriate, washed in TBST, and exposed overnight to rabbit antibodies to PTNR or mouse monoclonal antibodies to PTN (4B7). Antibodies were at a 1:20 dilution in PBS/0.1% Tween-20/1% BSA. As shown in FIG. 1(b), binding of the PTN protein to the recombinant extracellular domain (ECD) of ALK. The PTN or the ALK ECD protein were immobilized on nitrocellulose membranes. After incubation without (−) or with (+) ALK ECD or PTN, respectively, bound PTN or ALK ECD were visualized by immunodetection with the respective antibodies. Bound antibody was visualized using commercially available reagents (Souttou et al., 1997; Souttou et al., 1998). Further details of the experiments are as described (Stoica et al., 2001).

In this assay anti-PTN antibodies recognized PTN bound to the immobilized ALK and, conversely, anti-ALK ECD antibodies recognized ALK that was bound to immobilized PTN. These data strongly support the notion that ALK and PTN can bind to each other. Still, it is possible that other molecules that are not detected by the immunodetection participate in this ligand/receptor interaction and are indeed major players. To alleviate this concern, an independent and alternative approach was used to monitor ALK binding and probed for the binding of PTN to its receptor by protein chip technology coupled to mass spectrometry.

Example 3

Protein Chip Technology to Study PTN/receptor Binding

To obtain the most convincing data from the protein chip technology, ligand, PTN, was spiked into a mixture of proteins to render it barely detectable by mass spectrometry (FIG. 1c; input). In this manner, it was reasoned that ligand could be recovered if the ligand/bait interaction is specific and of high affinity. This approach would also show whether other proteins bound to the immobilized ALK receptor at an equimolar or even higher amount than the proposed ligand, PTN. Analysis was performed with a SELDI (surface-enhanced laser desorption/ionization) (Dove, 1999) Protein Biology System I (Ciphergen, Palo Alto, Calif.). Different PTN-containing ligand preparations (1 µl of a 20 µg/ml solution) were placed on a normal-phase protein array, which was then washed and 1 µl of cyano-4-hydroxy cinnamic acid (2 mg/ml) in 50%(v/v) acetonitrile and 0.5%(w/v) trifluoroacetic acid was added to the spot. Retained proteins were then subjected to mass spectrometry. For the analysis of the interaction of PTN with PTNR, 3 µl of a 240 µg/ml solution of either the Fc PTNR ECD (see above) or the human TGF-beta receptor II (Sigma) in phosphate-buffered saline (PBS) were applied to a preactivated protein array, which was then incubated overnight in a humidified chamber at 4° C. Protein solution was removed, 3 µl of 1 M ethanolamine (pH 8.2) were added to each spot, and the array was incubated for an additional 30 min at room temperature. PTN (20 µg/ml), either alone or in the presence of the PTNR ECD or TGF-beta receptor II each at a molar ratio of 1:1.7 relative to PTN, was dissolved in PBS containing 0.1% Triton X-100, and 3 µl of each solution were added to the appropriate spots. After incubation of the chips for 1 hour at room temperature in a humidified chamber, each spot was washed three times with 5 µl of PBS containing 0.1% Triton X-100, and the entire array was then washed once with 10ml of 25%(v/v) ethylene glycol and twice with 10 ml of PBS. Proteins were then analyzed by mass spectrometry (Stoica et al., 2001).

As shown in FIG. 1d, surface-enhanced laser desorption/ionization (SELDI) analysis (Dove, 1999) of PTN ligand binding to the ALK ECD was used. Mass spectrometry analysis of the "input" ligand preparation as well as of proteins bound to the immobilized ALK ECD or to a nonspecific protein control are shown. The arrowheads indicate the mass spectrometry position of the peak corresponding to the PTN protein. Proteins present in conditioned media ("input") bound to immobilized TGF-b RII (nonspecific) or to the immobilized ALK ECD. After subtraction of nonspecific binding only the peak indicated by the arrowhead remained (FIG. 1d). The ligand preparation ("input", upper panel) was incubated with the TGF-b RII protein as a control competitor (middle panel) or with the ALK ECD as a specific competitor (lower panel) and then allowed to bind to the immobilized ALK ECD (FIG. 1d). Analysis of bound proteins after SELDI shows that PTN binds to the immobilized ALK ECD and that this binding is competed by pre-incubation of the ligand solution with the ALK ECD.

The only specifically bound protein isolated from this was PTN (compare FIG. 2a: nonspecific versus ALK ECD binding). As a further series of control experiments a more purified PTN preparation (input) was used and showed a mass of 15,868 daltons for PTN. This mass was indistinguishable from the mass of the bound ligand obtained from binding studies to the ALK ECD using different PTN preparations (15882±43, n=4). Finally, it was also demonstrated that PTN binding to the immobilized ALK ECD was competed specifically by the presence of soluble ALK ECD in the incubation mixture (FIG. 2b). As a control, an unrelated recombinant receptor protein (TGF-beta receptor II) was unable to compete.

Example 4

PTN Receptor Binding Studies in Intact Cells

Beyond the binding studies in the cell-free system, ligand receptor binding was studied in cultured cells to prove that the interaction also occurred in vivo. For this, ALK-negative mouse hematopoietic cell line 32D was used which grows in suspension culture and expressed the ALK protein in these cells. Also used was $^{35}$S-labeled PTN from metabolic labeling experiments as a ligand for the receptor binding studies. Briefly, cell lysates were then prepared and a total of 3 mg of cellular proteins subjected to immunoprecipitation as described. (Souttou et al., 1997). For uncoupled antibodies, Sepharose-bound protein G (Gammabind plus, Amersham/Pharmacia) was used to precipitate immunocomplexes. Antibodies were anti-phosphotyrosine (agarose-coupled 4G10, 30 µl; UBI, Lake Placid NY), anti-PTNR (a cocktail of antibodies from Santa Cruz Biotechnology, Santa Cruz Calif. and from Accurate Chemicals, Westburg N.Y.), anti-IRS-1 (3 µg of rabbit IgG). Resulting precipitates were analyzed by SDS polyacrylamide gel electrophoresis. Experimental procedures for immunoblots for phosphotyrosine, IRS-1 (anti-IRS-1, Transduction Laboratories, Lexington Ky.), PLC-gamma (anti-PLC-gamma, UBI)and PI3-kinase (UBI) using unlabelled cells as described (Souttou et al., 1997).

Figure 2:
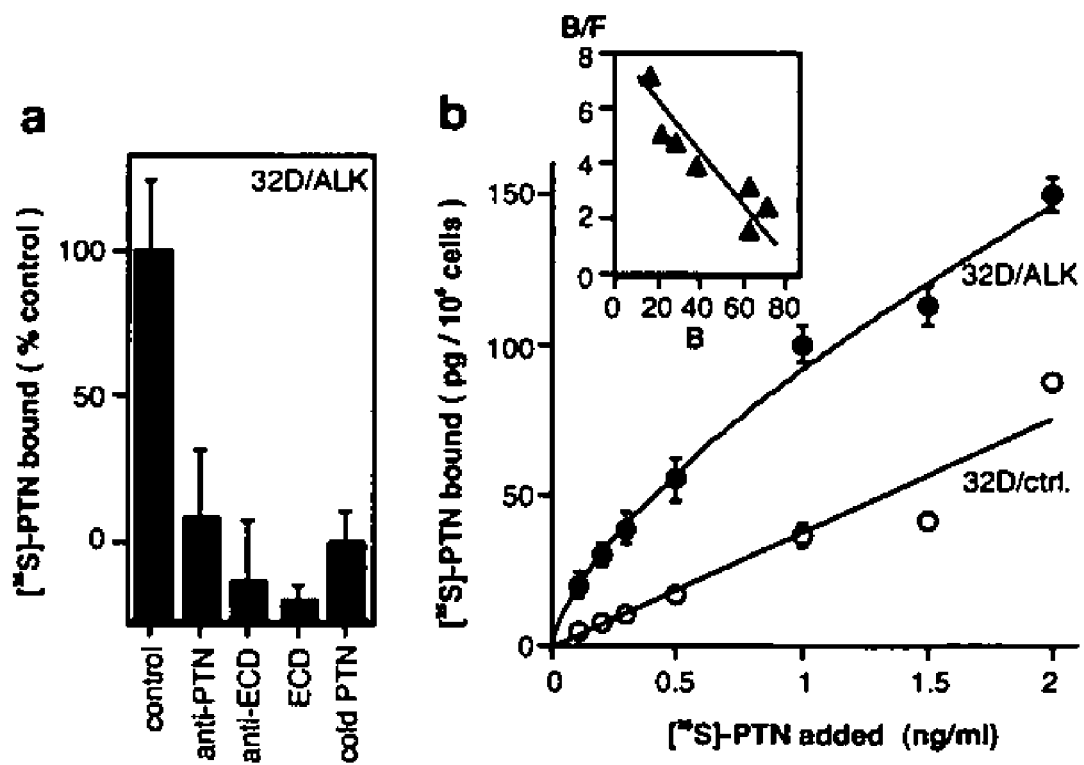
FIG. 2 (a) Competition of PTN binding to 32D/ALK-transfected cells, and (b) saturation binding of PTN to 32D/ALK and 32D/control cells.

As shown in FIG. 2, competition for the binding of radiolabeled PTN (1 ng/ml) to 32D/ALK-transfected cells by cold PTN (30X), ALK ECD protein (0.7 g/ml) or an affinity-purified anti-PTN antibody (2.5 g/ml) or an IgG raised against an ECD fragment containing the ligand binding domain (6 µg/ml) (FIG. 2a). Saturation binding of radiolabeled PTN to 32D/ALK (filled symbols) and 32D/control cells (open symbols) (FIG. 2b). Data were pooled from two independent experiments with triplicate repeat measurements of data points. Fitted curves were obtained from non-linear regression analysis for saturation binding studies (Prism-Graphpad). A Kd-value of 32+9 pM was calculated from this. Inset: Scatchard transformation of the binding data. B is specific binding, i.e. the difference between binding to 32D/ALK and 32D/control cells; F refers to the free concentration of PTN.

These studies showed saturable binding to the cells when they expressed the ALK cDNA and only non-specific, linearly increasing binding without the receptor present (FIG. 2b). Quantitation of these binding studies yielded an apparent dissociation constant of 30 to 40 pM, in close agreement with the effective concentrations of PTN in biological assays, i.e. in the 0.5 to 1 ng/ml range (Fang et al., 1992; Wellstein et al., 1992). Finally, in support of the specificity of the ligand/receptor interaction, PTN receptor binding was competed by anti-PTN and anti-ALK ECD antibodies as well as by added recombinant ALK ECD protein and unlabeled PTN (FIG. 3a). In summary, these data confirm that the ALK ECD recognizes and binds PTN as a ligand also in intact cells.

Example 5

PTN Signal Transduction Through the ALK Receptor

Figure 3:
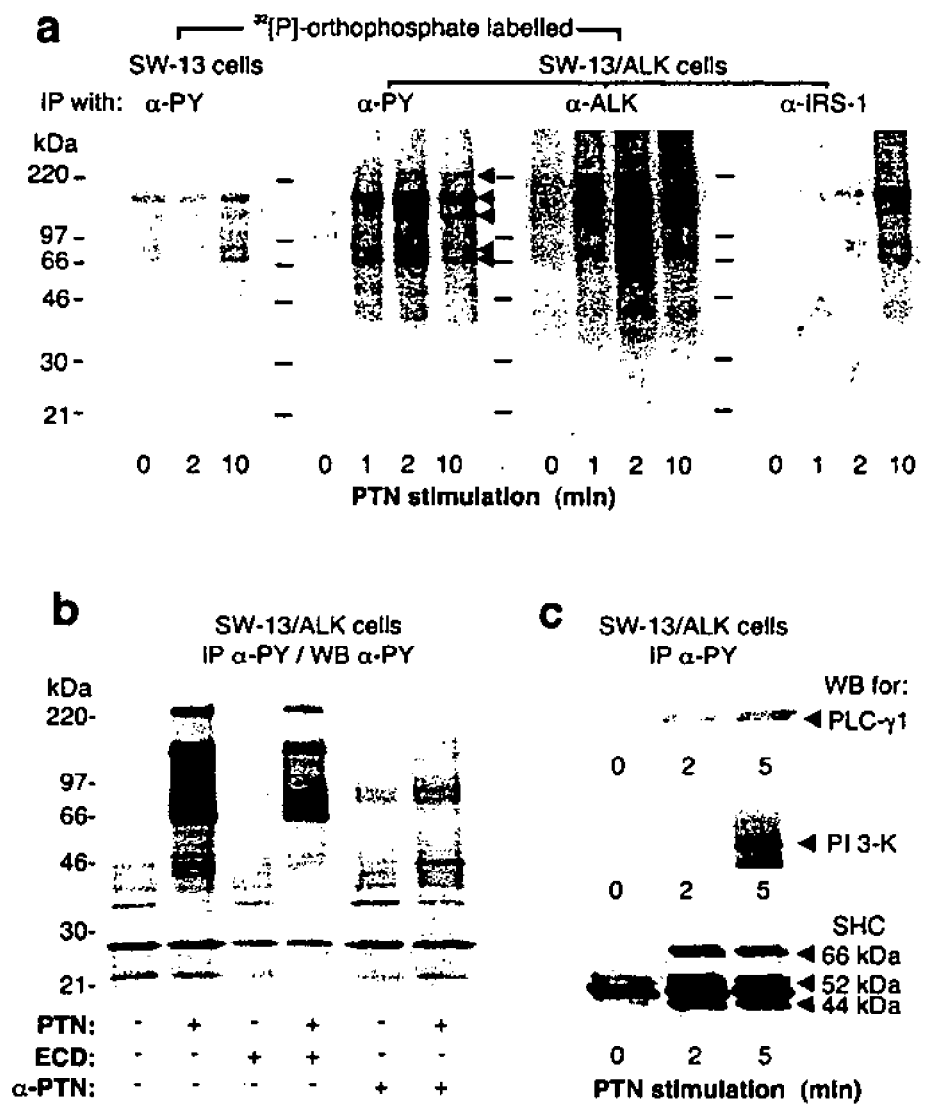
FIG. 3 (a) SW-13 or SW-13/ALK cells stimulated with PTN and immunoprecipitated with anti-PY, anti-ALK, or anti-IRS-1 antibodies. (b) SW-13/ALK cells stimulated with PTN, ECD or anti-PTN and immunoprecipitated with anti-PY or WB anti-PTN. (c) PTN stimulation of SW-13/ALK cells immunoprecipitated with anti-PY.

ALK receptor protein was over expressed in COS-7 and in SW-13 cells to study signal transduction. Sf-9 Drosophila melanogaster cells were cultured in EX-Cell 400 media (JRH Bioscience, Lenexa, Kans.), supplemented with 5% (v/v) fetal calf serum in a humidified incubator at 27° C. in the absence of $CO_2$. SW-13 cells have been used in a number of studies with PTN (Fang et al., 1992; Souttou et al., 1998; Wellstein et al., 1992). Stable transfection of SW-13 human adrenal carcinoma cells (Wellstein et al., 1992) was performed by electroporation. Further details are described in (Stoica et al., 2001). As shown in FIG. 3, ALK-transfected or control cells were grown in the presence of $^{32}$P-orthophosphate and stimulated with PTN. Protein extract was immunoprecipitated with different antibodies, separated by SDS-PAGE and the phosphoproteins were detected by autoradiography. Transient transfection of COS-7 cells stimulated with PTN without (+) and with fetal calf serum (++) for 5 min and immunoprecipitation with an anti-phosphotyrosine antibody (FIG. 3a). Immunoblot analysis for ALK showed equal expression in the ALK-transfected cells (not shown). Control SW-13 cells or SW-13/ALK stably transfected cells were stimulated with PTN for different time intervals as indicated and proteins immunoprecipitated with anti phosphotyrosine, anti-ALK or anti-IRS-1 antibodies (FIG. 3b). Effect of addition of the ALK ECD-Fc fusion protein (0.7 mg/ml) or an affinity-purified anti-PTN antibody (2.5 µg/ml) on PTN-induced tyrosine phosphorylation in SW-13/ALK cells (FIG. 3c). As under (FIG. 3b) SW-13/ALK cells were stimulated for 5 minutes with PTN that had been pre-incubated with anti-PTN or with the ALK ECD. The anti-phosphotyrosine Western blot (WB anti-PY) of immunoprecipitates with an anti-PY antibody (IP anti-PY) is shown.

Upon interaction of ALK with PTN, a series of proteins were found to be phosphorylated (FIGS. 3a, 3c). Phosphorylation was inhibited by the soluble ALK ECD and by antibodies against PTN (FIG. 3d). Key signal transduction molecules phosphorylated are IRS-1 (FIG. 3b), PLC-gamma, PI3-kinase and Shc (Stoica et al., 2001).

Example 6

ALK Expression in Human Tumor Cell Lines

Figure 4:
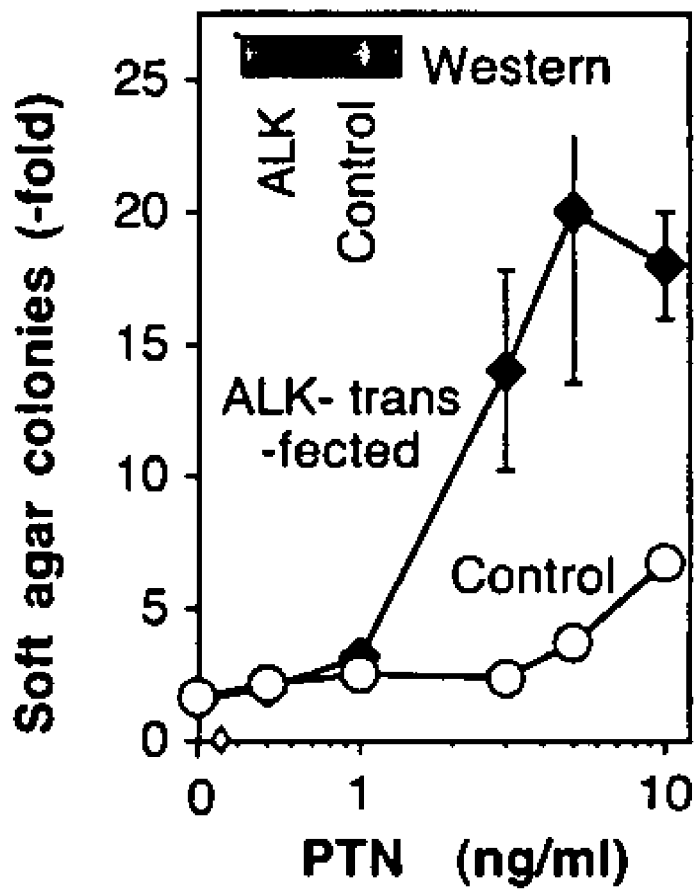
FIG. 4 Affect of ALK overexpression on PTN-stimulated growth.
Figure 5:
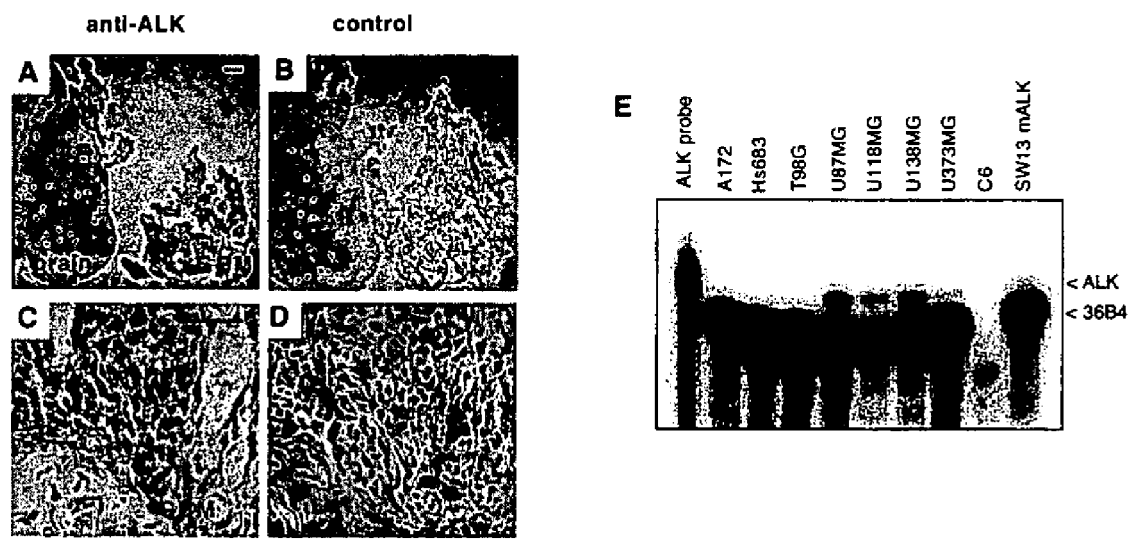
FIG. 5 (a-d) ALK expression in human GBM tissue and cell lines. (e) Detection of ALK mRNA in various cell lines by RNase protection.

Pleiotrophin is expressed at detectable levels in the normal adult nervous system and over expressed in brain tumors as well as in other cancers (Schulte et al., 1997). To evaluate the potential contribution of pleiotrophin signaling, expression of its receptor, ALK, in human glioblastoma samples and in tumor cell lines was examined. A dose-response relationship for the effect of PTN on colony formation in soft agar by SW-13/control and SW-13/ALK cells was determined. One representative of three independent experiments with mean ±S.E. of triplicate dishes is shown in FIG. 4. Inset: Western blot analysis for ALK protein in lysates of ALK-transfected or control SW-13 cells. For the tumor samples, immunohistochemistry was used to identify the ALK protein and assessed the expression relative to normal brain. Shown in FIG. 5 is ALK expression in human glioblastoma (GBM) tissue and cell lines. Detection of ALK protein in human glioblastoma tumor samples by immunohistochemistry (FIGS. 5a-d). Adjacent normal brain is negative for ALK protein by immunohistochemistry. The space bar equals 20 μm (FIG. 5e). Detection of human ALK mRNA in cell lines by RNase protection. Three of seven human glial cell lines (U87MG, U118MG and U138MG) are positive for ALK mRNA. C6 rat glioma and SW-13/mALK express rodent ALK MRNA and should not show cross-reactivity with the human ALK probe. 36B4 is a loading control.

Glioblastoma multiforme show a strong staining for ALK, whereas the signal was below detection in normal adjacent brain tissues (FIG. 5). This was confirmed in parallel experiments with four additional cases of glioblastoma (not shown). Anti-ALK antibodies raised against different antigens, i.e. the extracellular domain (ECD) of ALK and ECD-derived peptides gave the same distinctive result (not shown). In cultured cell lines, ALK MRNA was found expressed in three of seven human glioma or glioblastoma lines by RNase protection. A control for the specificity of the human ALK probe shows no cross-reaction with rodent ALK MRNA (C6 and SW-13/ murine ALK-transfected cells; FIG. 5e). Furthermore, pleiotrophin mRNA was found to be expressed in the ALK-positive cell lines (not shown) supporting a role of pleiotrophin as an autocrine as well as a paracine stimulator.

Example 7

PTN Signal Transduction in Glioblastoma Cells Via PI3-kinase

Figure 6:
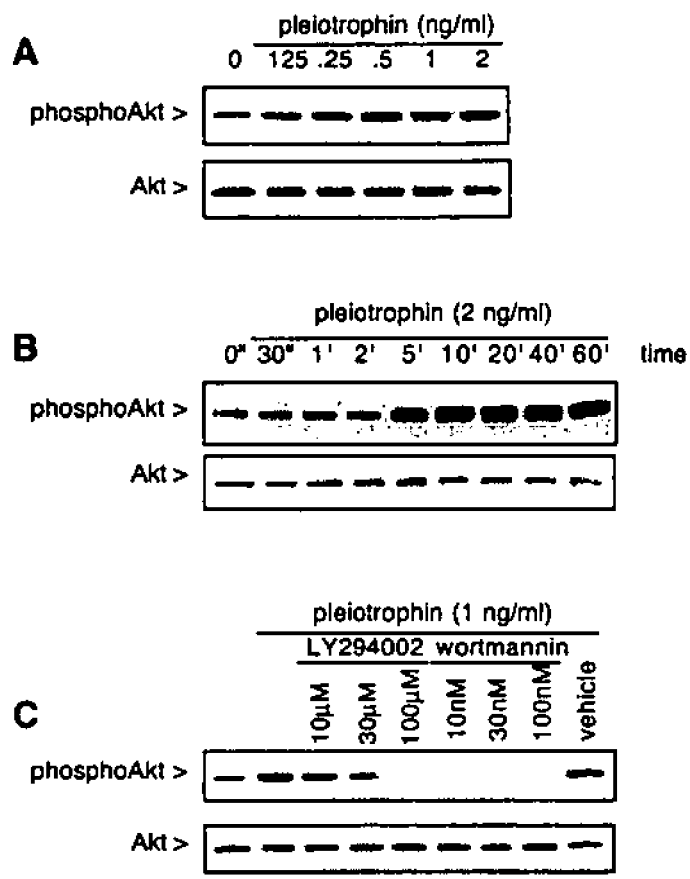
FIG. 6 (a-c) Pleiotrophin-induced AKT phosphorylation in U87MG cells.

The U87MG cell line was used to study the contribution of the pleiotrophin-ALK axis to the malignant phenotype of glioblastoma. U87MG cells are a well-characterized model system to study tumorigenesis and signaling in glioblastoma (Li et al., 1998; Wen et al., 2001) and express different receptor tyrosine kinases and their ligands such as EGF-R (O'Rourke et al., 1997) and PDGF-R (Nister et al., 1991). Furthermore, U87MG cells contain a mutated and inactive form of the tumor suppressor PTEN (exon 3) (Furnari et al., 1997; Maehama et al., 1999) and expression of an active form of PTEN suppresses their tumorigenicity and tumor angiogenesis (Li et al., 1998; Wen et al., 2001). The lipid phosphatase PTEN controls signaling pathways that involve PI3-kinase activity (Maehama et al., 1999) and was initially examined for pleiotrophin signals through PI3-kinase in the U87MG cells. For this phosphorylation of the downstream target molecule, Akt, was monitored an anti-apoptotic effector of PI3-kinase signaling that is activated by phosphorylation (Maehama et al., 1999; Khwaja, 1999). As shown in FIG. 6, pleiotrophin-induced Akt phosphorylation in U87MG cells. Representative immunoblots of the effects of pleiotrophin on Akt phosphorylation (on serine 473) in serum-starved wildtype U87MG cells: (FIG. 6a) Dose-response of pleiotrophin on Akt phosphorylation. (FIG. 6b) Time-course following treatment with 2 ng/ml pleiotrophin. (FIG. 6c) Inhibition by LY294002 and wortmannin of Akt phosphorylation in response to treatment with 1 ng/ml pleiotrophin. Akt protein blots are shown in the respective lower panels. Pleiotrophin induced Akt phosphorylation at Serine 473 in a dose-dependent manner and reached saturation at a very low concentration of the ligand (<1 ng/ml) after five minutes of treatment (FIG. 6a). The phosphorylation signal was maintained for at least one hour (FIG. 6b). The rapid response suggested that Akt phosphorylation is not due to a secondary effect of pleiotrophin signaling but rather due to a close link between pleiotrophin's activated receptor and P13-kinase. Pleiotrophin-induced Akt phosphorylation was inhibited by pretreatment of U87MG cells with the inhibitors LY294002 and wortmannin, confirming that this effect is indeed mediated by PI3-kinase (FIG. 6c). Interestingly, the MAP kinase pathway in the U87MG cells is activated constitutively and no increase in phosphorylation was observed after treatment with pleiotrophin (not shown). This suggested that the glioblastoma cells predominantly use the P13-kinase pathway for pleiotrophin-ALK signaling in contrast to epithelial cells in which ALK stimulation by pleiotrophin results in activation of both the MAPK and PI3-kinase pathways (Souttou et al., 1997; Stoica et al., 2001).

Example 8

Ribozyme-mediated Reduction of Endogenous ALK Reduces PTN Signaling

Figure 7:
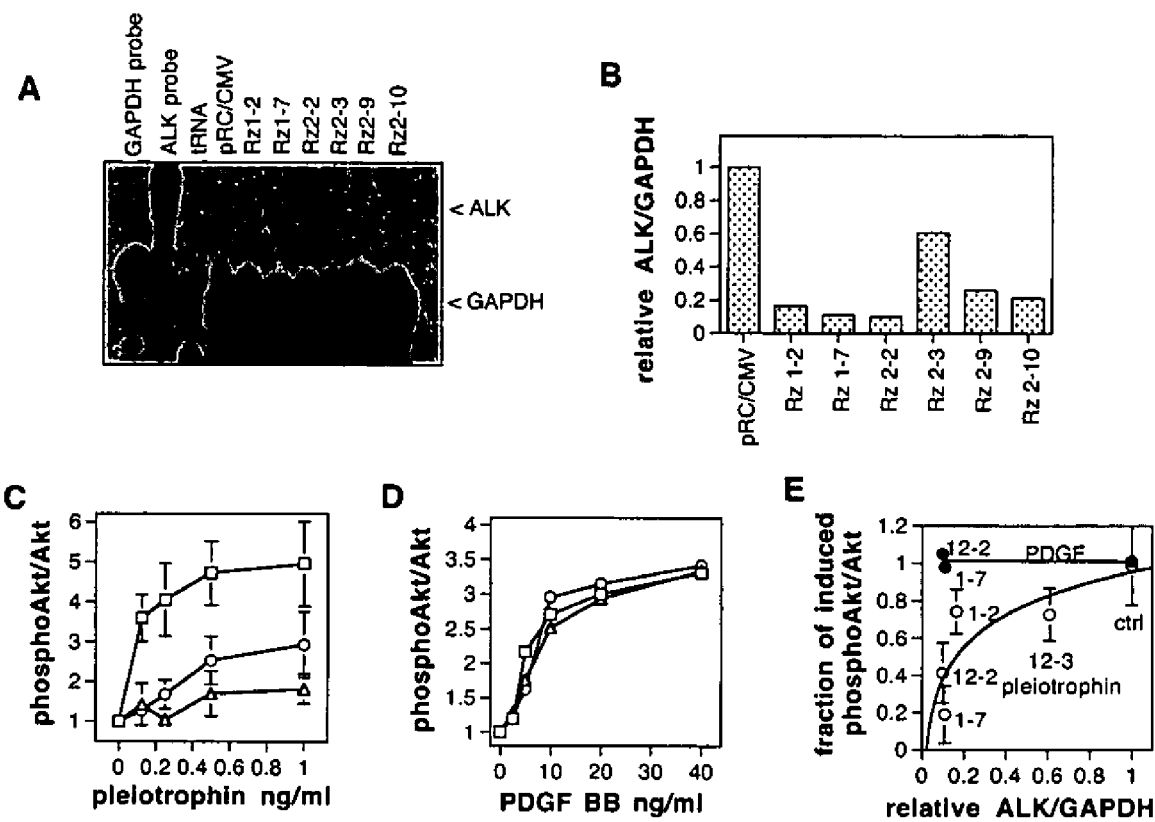
FIG. 7 (a) Autoradiogram and (b) quantitation by phospho-imager analysis of ALK mRNA. (c) Dose response of pleiotrophin, and (d) PDGF BB on phosphoAkt/Akt. (e) Comparison of the effect of PTN as a function of ALK levels in different cell lines.

To assess whether pleiotrophin signaling through ALK is rate-limiting for the malignant phenotype of U87MG cells, derivative cell lines were generated in which the endogenous ALK is reduced by constituitive expression of ALK MRNA targeted ribozymes. Shown in FIG. 7 is the effect of ALK depletion by ribozymes on pleiotrophin signaling. Detection of ALK mRNA by RNase protection assay in empty vector (pRC/CMV) and different ribozyme transfected U87MG cells. Autoradiogram (FIG. 7a) and quantitation by phosphoimager analysis (FIG. 7b); are shown relative to control (pRC/CMV). Dose-response of pleiotrophin (FIG. 7c) and PDGF BB (FIG. 7d) on pRC/CMV cells (squares), Rz1-7 cells (triangles) and Rz2-2 cells (circles). Comparison of the effect of pleiotrophin (0.5 ng/ml; open circles) or PDGF BB (20 ng/ml, closed circles) as a function of ALK levels in the different cell lines from panel (b) (FIG. 7e). Densitometric analyses of results of the immunoblots are presented as the mean of three independent experiments +/−S.E.M.

This approach has been applied to evaluate the contribution of different gene products to the malignant phenotype (Czubayko et al., 1994; Czubayko et al., 1996; Schulte et al., 1996; Czubayko et al., 1997; Wellstein et al., 1999) and initially screened different ALK-targeted ribozymes for their efficacy. From this, two ribozyme expression vectors were selected that target sequences in the 5' and in the 3' ends of the ALK mRNA (Rz1 and Rz2 respectively) and generated a panel of stably transfected U87MG cell lines with high, medium and low residual ALK mRNA levels (FIG. 7aand b). In these cell lines the ability of pleiotrophin to stimulate Akt phosphorylation was reduced in parallel with the reduced endogenous ALK mRNA (FIGS. 7c and e). In contrast, Akt phosphorylation induced through an independent tyrosine kinase receptor (PDGF-R) that is expressed in U87MG cells (Nister et al., 1991) was unaffected by the reduction of ALK (FIG. 7dand e). From these results, it was concluded that pleiotrophin's ability to induce Akt phosphorylation is strictly dependent on ALK.

Example 9

Reduction of ALK and Tumor Growth and Animal Survival

Figure 8:
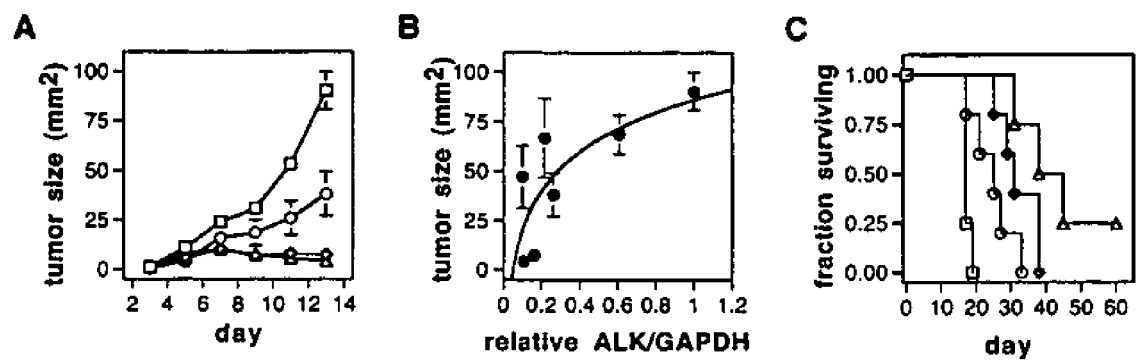
FIG. 8 Xenograft tumor growth showing (a) size and (b) relative ALK/GAPDH as a function of time after tumor cell inoculation. (c) Mice survival curves from panel (a).

Interestingly, the derivative U87MG cells with different residual levels of ALK showed no significant difference in their proliferation rate or colony formation in soft agar (not shown). This suggests that under in vitro growth conditions, ALK is not a rate-limiting factor. To determine if the reduction of pleiotrophin-ALK signaling affects the in vivo tumor growth of the U87MG cells, the different cell lines were grown as tumor xenografts in nude mice. As shown in FIG. 8, xenograft tumor growth (a) size of pRC/CMV (squares), Rz1-2 (diamonds), Rz1-7(triangles) and Rz2-9 (circles) xenograft tumors as a function of time after tumor cell inoculation. Tumor size of different cell lines at day thirteen as a function of relative ALK levels (FIG. 8*a*), and survival curves of mice from panel (a). Control cells with the highest residual levels of ALK formed rapidly growing tumors (FIG. 8*a*) at a rate that was indistinguishable from wild-type cells (not shown). In contrast, tumor growth of the ALK-depleted cells was significantly reduced (FIG. 8*a*). As with the responsiveness to pleiotrophin induction of Akt phosphorylation, the tumor size of the xenografts grown from the different cell lines was directly dependent on the level of ALK expression in a "gene-dose"-dependent manner (FIG. 8*b*). This "gene-dose" effect was observed with clonal and mass-transfected cell lines (not shown). Finally, the difference in tumor growth also resulted in a shift of the survival curve: while all of the control mice died by the twentieth day after injection, most mice injected with the ALK-depleted cells survived at least twice as long (FIG. 8*c*) and the median survival correlated with the residual ALK levels.

Example 10

ALK Levels and Mitotic Index and Apoptosis in Tumors

Figure 9:
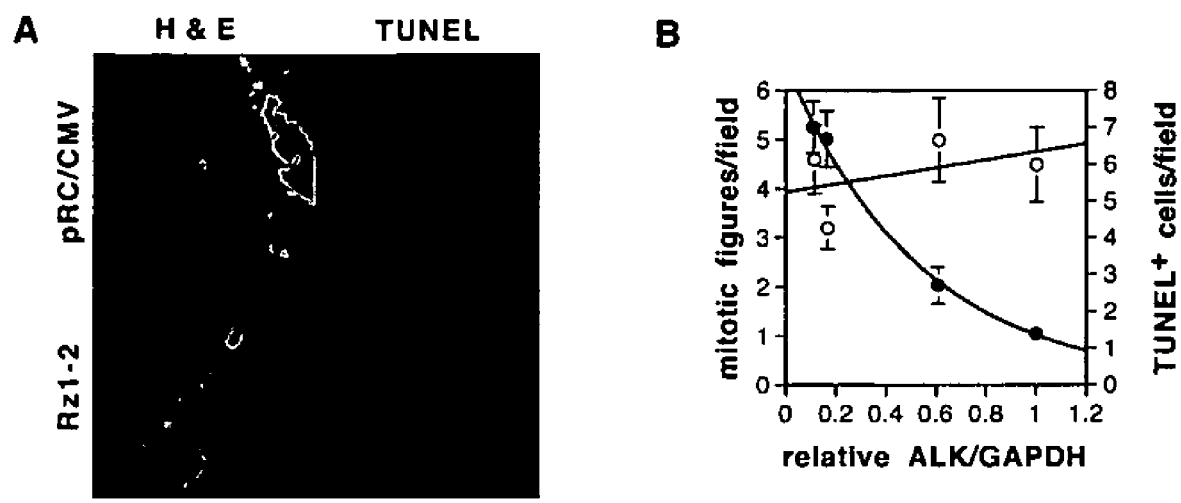
FIG. 9 Analysis of mitosis and apoptosis in tumor xenografts using (a) a high power (400X) H & E (left column) and TUNEL (right column) stained sections from size-matched pRC/CMV (upper row) and Rz1-2 (lower row) xenograft tumors. (b) Number of mitotic figures and TUNEL positive cells as a function of relative ALK levels.

In light of the fact that pleiotrophin signaling through ALK activates a pathway known to promote cell survival, namely P13-kinase and Akt, it was decided to investigate the rate of apoptosis in the xenograft tumor specimens and compare this to the mitotic index in the same samples. Using sections from size-matched tumors, H&E and TUNEL stained sections were examined for mitotic and apoptotic cells respectively (FIG. 9*a*). Analysis of mitosis and apoptosis in tumor xenografts using (a) a high power (400 x) H & E (left column) and TUNEL (right column) stained sections from size-matched pRC/CMV (upper row) and Rz1-2 (lower row) xenograft tumors, showing (b) the number of mitotic figures (open circles) and TUNEL positive cells (closed circles) as a function of relative ALK levels. Results are presented as the mean of twenty high power (400 x) fields +/−S.E.M.

No significant difference was found in the number of mitotic figures but a striking difference in the numbers of TUNEL positive cells. In fact, the number of TUNEL positive cells correlated directly with the reduction of ALK levels (FIG. 9*b*). Recent studies suggested a role of PTEN in tumor angiogenesis (Wen et al., 2001) and thus it was also assessed whether the reduction of ALK in the U87MG cells influenced the in vitro production of endothelial cell growth factors as well as the extent of tumor angiogenesis in vivo. Both, the endothelial cell growth-stimulatory activity present in the supernatants of the different U87MG cell lines as well as the extent of tumor angiogenesis measured in the tumor samples was not significantly affected by the reduction of ALK (not shown). Overall, these findings indicate that the pleiotrophin-ALK signaling provides an essential survival signal that is rate-limiting for tumor growth of U87MG cells.

Other embodiments and uses of the invention will be apparent to those skilled in the art from consideration of the specification and practice of the invention disclosed herein. All references cited herein, including all publications, U.S. and foreign patents and patent applications including U.S. provisional application number 60/211,491 entitled "Receptor for the Growth Factor PTN," filed Jun. 14, 2000, are specifically and entirely hereby incorporated herein by reference. It is intended that the specification and examples be considered exemplary only, with the true scope and spirit of the invention indicated by the following claims.

The invention claimed is:

1. A recombinant polypeptide comprising a pleiotrophin (PTN)-binding fragment of anaplastic lymphoma kinase (ALK), wherein the PTN-binding fragment consists of amino acid residues 368 to 447 of SEQ ID NO:2, and wherein said recombinant polypeptide does not comprise further regions of ALK.

2. The polypeptide of claim 1, wherein said polypeptide is soluble.

3. The polypeptide of claim 1 bound to PTN.

4. The polypeptide of claim 1 immobilized on a surface.

5. A. composition comprising the polypeptide of claim 1, further comprising a pharmaceutically acceptable carrier.

6. The composition of claim 5, further comprising PTN.

7. The recombinant polypeptide of claim 1, further comprising an Fc domain.

8. A composition comprising the peptide of claim 7, further comprising a pharmaceutically acceptable carrier.

9. The composition of claim 8, further comprising PTN.

* * * * *

```
                        SEQUENCE LISTING

<160> NUMBER OF SEQ ID NOS: 2

<210> SEQ ID NO 1
<211> LENGTH: 5293
<212> TYPE: DNA
<213> ORGANISM: Homo sapiens

<400> SEQUENCE: 1
agagacttgc gcgcacgcac agtcctctgg agatcaggtg gaaggagccg ctgggtacca        60
aggactgttc agagcctctt cccatctcgg ggagagcgaa gggtgaggct gggcccggag       120
agcagtgtaa acggcctcct ccggcgggat gggagccatc gggctcctgt ggctgctgcc       180
gctgctgctt tccacggcag ctgtgggctc cgggatgggg accggccagc gcgcgggctc       240
cccagctgcg gggccgccgc tgcagccccg ggagccactc agctactcgc gcctgcagag       300
gaagagtctg gcagttgact tcgtggtgcc ctcgctcttc cgtgtctacg cccgggacct       360
actgctgcca ccatcctcct cggagctgaa ggctggcagg cccgaggccc gcggctcgct       420
agctctggac tgcgcccgc tgctcaggtt gctggggccg gcgccggggg tctcctggac       480
```

-continued

```
cgccggttca ccagccccgg cagaggcccg gacgctgtcc agggtgctga agggcggctc    540
cgtgcgcaag ctccggcgtg ccaagcagtt ggtgctggag ctgggcgagg aggcgatctt    600
ggagggttgc gtcgggcccc ccggggaggc ggctgtgggg ctgctccagt tcaatctcag    660
cgagctgttc agttggtgga ttcgccaagg cgaagggcga ctgaggatcc gcctgatgcc    720
cgagaagaag gcgtcggaag tgggcagaga gggaaggctg tccgcggcaa ttcgcgcctc    780
ccagccccgc cttctcttcc agatcttcgg gactggtcat agctccttgg aatcaccaac    840
aaacatgcct tctccttctc ctgattattt tacatggaat ctcacctgga taatgaaaga    900
ctccttccct ttcctgtctc atcgcagccg atatggtctg gagtgcagct ttgacttccc    960
ctgtgagctg gagtattccc ctccactgca tgacctcagg aaccagagct ggtcctggcg   1020
ccgcatcccc tccgaggagg cctcccagat ggacttgctg gatgggcctg ggcagagcg   1080 ttctaaggag atgcccagag gctccttttct ccttctcaac acctcagctg actccaagca   1140
caccatcctg agtccgtgga tgaggagcag cagtgagcac tgcacactgg ccgtctcggt   1200
gcacaggcac ctgcagccct ctggaaggta cattgcccag ctgctgcccc acaacgaggc   1260
tgcaagagag atcctcctga tgcccactcc agggaagcat ggttggacag tgctccaggg   1320
aagaatcggg cgtccagaca acccatttcg agtggccctg aatacatct ccagtggaaa    1380 ccgcagcttg tctgcagtgg acttctttgc cctgaagaac tgcagtgaag gaacatcccc   1440
aggctccaag atggccctgc agagctcctt cacttgttgg aatgggacag tcctccagct   1500
tgggcaggcc tgtgacttcc accaggactg tgcccaggga gaagatgaga gccagatgtg   1560
ccggaaactg cctgtggggtt tttactgcaa cttttgaagat ggcttctgtg ctggaccca   1620 aggcacactg tcaccccaca ctcctcagtg gcaggtcagg accctaaagg atgcccggtt   1680
ccaggaccac caagaccatg ctctattgct cagtaccact gatgtccccg cttctgaaag   1740
tgctacagtg accagtgcta cgtttcctgc accgatcaag agctctccat gtgagctccg   1800
aatgtcctgg ctcattcgtg gagtcttgag gggaaacgtg tccttggtgc tagtggagaa   1860
caaaaccggg aaggagcaag gcaggatggt ctggcatgtc gccgcctatg aaggcttgag   1920
cctgtggcag tggatggtgt tgcctctcct cgatgtgtct gacaggttct ggctgcagat   1980
ggtcgcatgg tggggacaag gatccagagc catcgtggct tttgacaata tctccatcag   2040
cctggactgc tacctcacca ttagcggaga ggacaagatc ctgcagaata cagcacccaa   2100
atcaagaaac ctgtttgaga gaaacccaaa caaggagctg aaacccgggg aaaattcacc   2160
aagacagacc cccatctttg acctacagt tcattggctg ttcaccacat gtggggccag   2220
cgggccccat ggccccaccc aggcacagtg caacaacgcc taccagaact ccaacctgag   2280
cgtggaggtg gggagcgagg gcccctgaa aggcatccag atctgaagg tgccagccac   2340 cgacacctac agcatctcgg gctacggagc tgctggcggg aaaggcggga agaacaccat   2400
gatgcggtcc cacggcgtgt ctgtgctggg catcttcaac ctggagaagg atgacatgct   2460
gtacatcctg gttgggcagc agggagagga cgcctgcccc agtacaaacc agttaatcca   2520
gaaagtctgc attggagaga acaatgtgat agaagaagaa atccgtgtga acagaagcgt   2580
gcatgagtgg gcaggaggcg gaggaggagg gggtggagcc acctacgtat ttaagatgaa   2640
ggatggagtg ccggtgcccc tgatcattgc agccggaggt ggtggcaggg cctacggggc   2700
caagacagac acgttccacc cagagagact ggagaataac tcctcggttc tagggctaaa   2760
cggcaattcc ggagccgcag gtggtggagg tggctggaat gataacactt ccttgctctg   2820
ggccggaaaa tctttgcagg agggtgccac cggaggacat tcctgccccc aggccatgaa   2880
```

-continued

```
gaagtgggggg tgggagacaa gagggggttt cggagggggt ggaggggggt gctcctcagg    2940
tggaggaggc ggaggatata taggcggcaa tgcagcctca acaatgacc ccgaaatgga     3000
tggggaagat ggggtttcct tcatcagtcc actgggcatc ctgtacaccc cagctttaaa    3060
agtgatggaa ggccacgggg aagtgaatat taagcattat ctaaactgca gtcactgtga    3120
ggtagacgaa tgtcacatgg accctgaaag ccacaaggtc atctgcttct gtgaccacgg    3180
gacggtgctg gctgaggatg gcgtctcctg cattgtgtca cccaccccgg agccacacct    3240
gccactctcg ctgatcctct ctgtggtgac ctctgccctc gtggccgccc tggtcctggc    3300
tttctccggc atcatgattg tgtaccgccg gaagcaccag gagctgcaag ccatgcagat    3360
ggagctgcag agccctgagt acaagctgag caagctccgc acctcgacca tcatgaccga    3420
ctacaacccc aactactgct tgctggcaa gacctcctcc atcagtgacc tgaaggaggt    3480
gccgcggaaa aacatcaccc tcattcgggg tctgggccat ggcgcctttg ggaggtgta    3540
tgaaggccag gtgtccggaa tgcccaacga cccaagcccc ctgcaagtgg ctgtgaagac    3600
gctgcctgaa gtgtgctctg aacaggacga actggatttc ctcatggaag ccctgatcat    3660
cagcaaattc aaccaccaga acattgttcg ctgcattggg gtgagcctgc aatccctgcc    3720
ccggttcatc ctgctggagc tcatggcggg gggagacctc aagtccttcc tccgagagac    3780
ccgccctcgc ccgagccagc cctcctccct ggccatgctg gaccttctgc acgtggctcg    3840
ggacattgcc tgtggctgtc agtatttgga ggaaaaccac ttcatccacc gagacattgc    3900
tgccagaaac tgcctcttga cctgtccagg ccctggaaga gtggccaaga ttggagactt    3960
cgggatggcc cgagacatct acagggcgag ctactataga aagggaggct gtgccatgct    4020
gccagttaag tggatgccccc cagaggcctt catggaagga atattcactt ctaaaacaga    4080
cacatggtcc tttggagtgc tgctatggga aatctttttct cttggatata tgccataccc    4140
cagcaaaagc aaccaggaag ttctggagtt tgtcaccagt ggaggccgga tggacccacc    4200
caagaactgc cctgggcctg tataccggat aatgactcag tgctggcaac atcagcctga    4260
agacaggccc aactttgcca tcattttgga gaggattgaa tactgcaccc aggacccgga    4320
tgtaatcaac accgctttgc cgatagaata tggtccactt gtggaagagg aagagaaagt    4380
gcctgtgagg cccaaggacc ctgaggggggt tcctcctctc ctggtctctc aacaggcaaa    4440
acgggaggag gagcgcagcc cagctgcccc accacctctg cctaccacct cctctggcaa    4500
ggctgcaaag aaacccacag ctgcagaggt ctctgttcga gtcccctagag ggccggccgt    4560
ggaagggggga cacgtgaata tggcattctc tcagtccaac cctccttcgg agttgcacag    4620
ggtccacgga tccagaaata agcccaccag cttgtggaac ccaacgtacg gctcctggtt    4680
tacagagaaa cccaccaaaa agaataatcc tatagcaaag aaggagccac acgagagggg    4740
taacctgggg ctggagggaa gctgtactgt cccacctaac gttgcaactg ggagacttcc    4800
gggggcctca ctgctcctag agccctcttc gctgactgcc aatatgaagg aggtacctct    4860
gttcaggcta cgtcacttcc cttgtgggaa tgtcaattac ggctaccagc aacagggctt    4920
gcccttagaa gccgctactg cccctggagc tggtcattac gaggatacca ttctgaaaag    4980
caagaatagc atgaaccagc ctgggccctg agctcggtcg cacactcact tctcttcctt    5040
gggatcccta agaccgtgga ggagagagag gcaatcaatg gctcctttca caaaccagag    5100
accaaatgtc acgttttgtt ttgtgccaac ctatttgaa gtaccaccaa aaaagctgta    5160
ttttgaaaat gctttagaaa ggttttgagc atgggttcat cctattcttt cgaaagaaga    5220
```

```
aaatatcata aaaatgagtg ataaatacaa ggccagatgt ggttgcataa ggttttatg    5280 catgtttgtt gta                                                      5293
```

<210> SEQ ID NO 2
<211> LENGTH: 1620
<212> TYPE: PRT
<213> ORGANISM: Homo sapiens

<400> SEQUENCE: 2

```
Met Gly Ala Ile Gly Leu Leu Trp Leu Leu Pro Leu Leu Ser Thr
 1               5                  10                  15

Ala Ala Val Gly Ser Gly Met Gly Thr Gly Gln Arg Ala Gly Ser Pro
             20                  25                  30

Ala Ala Gly Pro Pro Leu Gln Pro Arg Glu Pro Leu Ser Tyr Ser Arg
         35                  40                  45

Leu Gln Arg Lys Ser Leu Ala Val Asp Phe Val Pro Ser Leu Phe
 50                  55                  60

Arg Val Tyr Ala Arg Asp Leu Leu Leu Pro Ser Ser Ser Glu Leu
 65                  70                  75                  80

Lys Ala Gly Arg Pro Glu Ala Arg Gly Ser Leu Ala Leu Asp Cys Ala
             85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
    290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
            340                 345                 350

Arg His Leu Gln Pro Ser Gly Arg Tyr Ile Ala Gln Leu Leu Pro His
```

-continued

```
              355                 360                 365
Asn Glu Ala Ala Arg Glu Ile Leu Leu Met Pro Thr Pro Gly Lys His
            370                 375                 380
Gly Trp Thr Val Leu Gln Gly Arg Ile Gly Arg Pro Asp Asn Pro Phe
385                 390                 395                 400
Arg Val Ala Leu Glu Tyr Ile Ser Ser Gly Asn Arg Ser Leu Ser Ala
                405                 410                 415
Val Asp Phe Phe Ala Leu Lys Asn Cys Ser Glu Gly Thr Ser Pro Gly
                420                 425                 430
Ser Lys Met Ala Leu Gln Ser Ser Phe Thr Cys Trp Asn Gly Thr Val
            435                 440                 445
Leu Gln Leu Gly Gln Ala Cys Asp Phe His Gln Asp Cys Ala Gln Gly
        450                 455                 460
Glu Asp Glu Ser Gln Met Cys Arg Lys Leu Pro Val Gly Phe Tyr Cys
465                 470                 475                 480
Asn Phe Glu Asp Gly Phe Cys Gly Trp Thr Gln Gly Thr Leu Ser Pro
                485                 490                 495
His Thr Pro Gln Trp Gln Val Arg Thr Leu Lys Asp Ala Arg Phe Gln
            500                 505                 510
Asp His Gln Asp His Ala Leu Leu Leu Ser Thr Thr Asp Val Pro Ala
        515                 520                 525
Ser Glu Ser Ala Thr Val Thr Ser Ala Thr Phe Pro Ala Pro Ile Lys
    530                 535                 540
Ser Ser Pro Cys Glu Leu Arg Met Ser Trp Leu Ile Arg Gly Val Leu
545                 550                 555                 560
Arg Gly Asn Val Ser Leu Val Leu Val Glu Asn Lys Thr Gly Lys Glu
                565                 570                 575
Gln Gly Arg Met Val Trp His Val Ala Ala Tyr Glu Gly Leu Ser Leu
            580                 585                 590
Trp Gln Trp Met Val Leu Pro Leu Leu Asp Val Ser Asp Arg Phe Trp
        595                 600                 605
Leu Gln Met Val Ala Trp Trp Gly Gln Gly Ser Arg Ala Ile Val Ala
    610                 615                 620
Phe Asp Asn Ile Ser Ile Ser Leu Asp Cys Tyr Leu Thr Ile Ser Gly
625                 630                 635                 640
Glu Asp Lys Ile Leu Gln Asn Thr Ala Pro Lys Ser Arg Asn Leu Phe
                645                 650                 655
Glu Arg Asn Pro Asn Lys Glu Leu Lys Pro Gly Glu Asn Ser Pro Arg
            660                 665                 670
Gln Thr Pro Ile Phe Asp Pro Thr Val His Trp Leu Phe Thr Thr Cys
        675                 680                 685
Gly Ala Ser Gly Pro His Gly Pro Thr Gln Ala Gln Cys Asn Asn Ala
    690                 695                 700
Tyr Gln Asn Ser Asn Leu Ser Val Glu Val Gly Ser Glu Gly Pro Leu
705                 710                 715                 720
Lys Gly Ile Gln Ile Trp Lys Val Pro Ala Thr Asp Thr Tyr Ser Ile
                725                 730                 735
Ser Gly Tyr Gly Ala Ala Gly Gly Lys Gly Gly Lys Asn Thr Met Met
            740                 745                 750
Arg Ser His Gly Val Ser Val Leu Gly Ile Phe Asn Leu Glu Lys Asp
        755                 760                 765
Asp Met Leu Tyr Ile Leu Val Gly Gln Gln Gly Glu Asp Ala Cys Pro
    770                 775                 780
```

-continued

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
            805                 810                 815

Gly Gly Gly Gly Gly Gly Ala Thr Tyr Val Phe Lys Met Lys Asp
        820                 825                 830

Gly Val Pro Val Pro Leu Ile Ile Ala Ala Gly Gly Gly Arg Ala
        835                 840                 845

Tyr Gly Ala Lys Thr Asp Thr Phe His Pro Glu Arg Leu Glu Asn Asn
850                 855                 860

Ser Ser Val Leu Gly Leu Asn Gly Asn Ser Gly Ala Ala Gly Gly Gly
865                 870                 875                 880

Gly Gly Trp Asn Asp Asn Thr Ser Leu Leu Trp Ala Gly Lys Ser Leu
            885                 890                 895

Gln Glu Gly Ala Thr Gly Gly His Ser Cys Pro Gln Ala Met Lys Lys
        900                 905                 910

Trp Gly Trp Glu Thr Arg Gly Gly Phe Gly Gly Gly Gly Gly Cys
        915                 920                 925

Ser Ser Gly Gly Gly Gly Gly Gly Tyr Ile Gly Gly Asn Ala Ala Ser
930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
            965                 970                 975

Gly Glu Val Asn Ile Lys His Tyr Leu Asn Cys Ser His Cys Glu Val
        980                 985                 990

Asp Glu Cys His Met Asp Pro Glu Ser His Lys Val Ile Cys Phe Cys
        995                 1000                1005

Asp His Gly Thr Val Leu Ala Glu Asp Gly Val Ser Cys Ile Val Ser
    1010                1015                1020

Pro Thr Pro Glu Pro His Leu Pro Leu Ser Leu Ile Leu Ser Val Val
1025                1030                1035                1040

Thr Ser Ala Leu Val Ala Ala Leu Val Leu Ala Phe Ser Gly Ile Met
                1045                1050                1055

Ile Val Tyr Arg Arg Lys His Gln Glu Leu Gln Ala Met Gln Met Glu
            1060                1065                1070

Leu Gln Ser Pro Glu Tyr Lys Leu Ser Lys Leu Arg Thr Ser Thr Ile
        1075                1080                1085

Met Thr Asp Tyr Asn Pro Asn Tyr Cys Phe Ala Gly Lys Thr Ser Ser
        1090                1095                1100

Ile Ser Asp Leu Lys Glu Val Pro Arg Lys Asn Ile Thr Leu Ile Arg
1105                1110                1115                1120

Gly Leu Gly His Gly Ala Phe Gly Glu Val Tyr Glu Gly Gln Val Ser
                1125                1130                1135

Gly Met Pro Asn Asp Pro Ser Pro Leu Gln Val Ala Val Lys Thr Leu
            1140                1145                1150

Pro Glu Val Cys Ser Glu Gln Asp Glu Leu Asp Phe Leu Met Glu Ala
        1155                1160                1165

Leu Ile Ile Ser Lys Phe Asn His Gln Asn Ile Val Arg Cys Ile Gly
        1170                1175                1180

Val Ser Leu Gln Ser Leu Pro Arg Phe Ile Leu Leu Glu Leu Met Ala
1185                1190                1195                1200

-continued

```
Gly Gly Asp Leu Lys Ser Phe Leu Arg Glu Thr Arg Pro Arg Pro Ser
            1205                1210                1215

Gln Pro Ser Ser Leu Ala Met Leu Asp Leu Leu His Val Ala Arg Asp
        1220                1225                1230

Ile Ala Cys Gly Cys Gln Tyr Leu Glu Glu Asn His Phe Ile His Arg
        1235                1240                1245

Asp Ile Ala Ala Arg Asn Cys Leu Leu Thr Cys Pro Gly Pro Gly Arg
    1250                1255                1260

Val Ala Lys Ile Gly Asp Phe Gly Met Ala Arg Asp Ile Tyr Arg Ala
1265                1270                1275                1280

Ser Tyr Tyr Arg Lys Gly Gly Cys Ala Met Leu Pro Val Lys Trp Met
                1285                1290                1295

Pro Pro Glu Ala Phe Met Glu Gly Ile Phe Thr Ser Lys Thr Asp Thr
                1300                1305                1310

Trp Ser Phe Gly Val Leu Leu Trp Glu Ile Phe Ser Leu Gly Tyr Met
                1315                1320                1325

Pro Tyr Pro Ser Lys Ser Asn Gln Glu Val Leu Glu Phe Val Thr Ser
            1330                1335                1340

Gly Gly Arg Met Asp Pro Pro Lys Asn Cys Pro Gly Pro Val Tyr Arg
1345                1350                1355                1360

Ile Met Thr Gln Cys Trp Gln His Gln Pro Glu Asp Arg Pro Asn Phe
                1365                1370                1375

Ala Ile Ile Leu Glu Arg Ile Glu Tyr Cys Thr Gln Asp Pro Asp Val
            1380                1385                1390

Ile Asn Thr Ala Leu Pro Ile Glu Tyr Gly Pro Leu Val Glu Glu Glu
            1395                1400                1405

Glu Lys Val Pro Val Arg Pro Lys Asp Pro Glu Gly Val Pro Pro Leu
        1410                1415                1420

Leu Val Ser Gln Gln Ala Lys Arg Glu Glu Glu Arg Ser Pro Ala Ala
1425                1430                1435                1440

Pro Pro Pro Leu Pro Thr Thr Ser Ser Gly Lys Ala Ala Lys Lys Pro
                1445                1450                1455

Thr Ala Ala Glu Val Ser Val Arg Val Pro Arg Gly Pro Ala Val Glu
                1460                1465                1470

Gly Gly His Val Asn Met Ala Phe Ser Gln Ser Asn Pro Pro Ser Glu
            1475                1480                1485

Leu His Arg Val His Gly Ser Arg Asn Lys Pro Thr Ser Leu Trp Asn
        1490                1495                1500

Pro Thr Tyr Gly Ser Trp Phe Thr Glu Lys Pro Thr Lys Lys Asn Asn
1505                1510                1515                1520

Pro Ile Ala Lys Lys Glu Pro His Glu Arg Gly Asn Leu Gly Leu Glu
                1525                1530                1535

Gly Ser Cys Thr Val Pro Pro Asn Val Ala Thr Gly Arg Leu Pro Gly
            1540                1545                1550

Ala Ser Leu Leu Leu Glu Pro Ser Ser Leu Thr Ala Asn Met Lys Glu
            1555                1560                1565

Val Pro Leu Phe Arg Leu Arg His Phe Pro Cys Gly Asn Val Asn Tyr
        1570                1575                1580

Gly Tyr Gln Gln Gln Gly Leu Pro Leu Glu Ala Ala Thr Ala Pro Gly
1585                1590                1595                1600
```

-continued

```
Ala Gly His Tyr Glu Asp Thr Ile Leu Lys Ser Lys Asn Ser Met Asn
                1605                1610                1615

Gln Pro Gly Pro
        1620
```